US010174372B2

(12) United States Patent
Kester

(10) Patent No.: US 10,174,372 B2
(45) Date of Patent: Jan. 8, 2019

(54) PRESERVATION OF INFORMATION RELATED TO GENOMIC DNA METHYLATION

(71) Applicant: Illumina, Inc., San Diego, CA (US)

(72) Inventor: Henri A. Kester, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 122 days.

(21) Appl. No.: 15/469,811

(22) Filed: Mar. 27, 2017

(65) Prior Publication Data

US 2017/0260581 A1 Sep. 14, 2017

Related U.S. Application Data

(60) Division of application No. 14/327,892, filed on Jul. 10, 2014, now Pat. No. 9,605,311, which is a continuation of application No. 14/020,241, filed on Sep. 6, 2013, now Pat. No. 8,895,268, which is a division of application No. 13/125,419, filed as application No. PCT/US2009/061552 on Oct. 21, 2009, now Pat. No. 8,541,207.

(60) Provisional application No. 61/107,457, filed on Oct. 22, 2008.

(51) Int. Cl.
| C12P 19/34 | (2006.01) |
| C12Q 1/6874 | (2018.01) |
| C12Q 1/6855 | (2018.01) |
| C12Q 1/6858 | (2018.01) |
| C12Q 1/6876 | (2018.01) |

(52) U.S. Cl.
CPC ......... *C12Q 1/6874* (2013.01); *C12Q 1/6855* (2013.01); *C12Q 1/6858* (2013.01); *C12Q 1/6876* (2013.01); *C12Q 2600/156* (2013.01)

(58) Field of Classification Search
CPC ............ C12Q 1/6858; C12Q 2523/125; C12Q 2535/119; C12Q 1/6855; C12Q 2525/117; C12Q 2525/125; C12Q 2525/191; C12Q 1/6874; C12Q 2525/301; C12Q 1/6876
USPC ....................................................... 435/91.2
See application file for complete search history.

(56) References Cited

U.S. PATENT DOCUMENTS

| 5,302,509 | A | 4/1994 | Cheeseman |
| 5,786,146 | A | 7/1998 | Herman |
| 5,871,917 | A | 2/1999 | Duffy |
| 6,200,756 | B1 | 3/2001 | Herman |
| 6,214,556 | B1 | 4/2001 | Olek |
| 6,251,594 | B1 | 6/2001 | Gonzalgo |
| 6,265,171 | B1 | 7/2001 | Herman |
| 6,300,071 | B1 | 10/2001 | Vuylsteke |
| 6,306,597 | B1 | 10/2001 | Macevicz |
| 6,331,393 | B1 | 12/2001 | Laird |
| 6,605,432 | B1 | 8/2003 | Huang |
| 6,720,179 | B1 | 4/2004 | Macevicz |
| 7,057,026 | B2 | 6/2006 | Barnes |
| 7,232,656 | B2 | 6/2007 | Balasubramanian |
| 7,598,035 | B2 | 10/2009 | Macevicz |
| 7,611,869 | B2 | 11/2009 | Fan |
| 2002/0086324 | A1 | 7/2002 | Laird |
| 2002/0137056 | A1 | 9/2002 | Olek |
| 2002/0137086 | A1 | 9/2002 | Olek |
| 2003/0022207 | A1 | 1/2003 | Balasubramanian |
| 2003/0082600 | A1 | 5/2003 | Olek |
| 2003/0119025 | A1 | 6/2003 | Olek |
| 2003/0129620 | A1 | 7/2003 | Olek |
| 2003/0162194 | A1 | 8/2003 | Olek |
| 2003/0170684 | A1 | 9/2003 | Fan |
| 2004/0023230 | A1 | 2/2004 | Olek |
| 2004/0072197 | A1 | 4/2004 | Jones |
| 2004/0106110 | A1 | 6/2004 | Balasubramanian |
| 2004/0234960 | A1 | 11/2004 | Olek |
| 2004/0248090 | A1 | 12/2004 | Olek |
| 2004/0265814 | A1 | 12/2004 | Distler |
| 2005/0019762 | A1 | 1/2005 | Olek |
| 2005/0042649 | A1 | 2/2005 | Balasubramanian |
| 2005/0053937 | A1 | 3/2005 | Berlin |
| 2005/0196792 | A1* | 9/2005 | Fodor .................. C12Q 1/6827 435/6.12 |
| 2007/0122818 | A1 | 5/2007 | Mazumder |
| 2008/0051294 | A1 | 2/2008 | Gormley |
| 2008/0108073 | A1 | 5/2008 | Nautiyal |
| 2010/0167954 | A1 | 7/2010 | Earnshaw |
| 2010/0311597 | A1 | 12/2010 | Swerdlow |

FOREIGN PATENT DOCUMENTS

| EP | 1790736 | 5/2007 |
| WO | WO 1991/06678 | 5/1991 |
| WO | WO 1998/13523 | 4/1998 |
| WO | WO 1998/86952 | 12/1998 |
| WO | WO 200/06770 | 2/2000 |

(Continued)

OTHER PUBLICATIONS

Baylin, et al., "DNA hypermethylation in tumorigenesis: epigenetics joins genetics", Trends Genet., 16(4 ), 2000, 168-174.
Bentley, "Whole-genome re-sequencing", Curr. Opin. Genet. Dev. No. 16 (6), 2006, 545-52.
Bestor, "Gene silencing. Methylation meets acetylation", Nature, 393 (6683), 1998, 311-312.
Bibikova, et al., "High-throughput DNA methylation profiling using universal bead arrays", Genome Research, 16, 2006, 383-393.
Costello, et al., "Aberrant CpG-Island methylation has non-random and tumour-type-specific patterns", Nat Genet 24(2):132-138 (2000), 2000, 032-138.

(Continued)

*Primary Examiner* — Cynthia B Wilder
(74) *Attorney, Agent, or Firm* — Knobbe, Martens, Olson & Bear LLP

(57) ABSTRACT

The present invention relates to compositions, methods and systems for analyzing the methylation state of nucleic acids. Some embodiments relate to a compositions, methods and systems for analyzing the methylation state of DNA with a gene array.

20 Claims, 12 Drawing Sheets

(56) References Cited

FOREIGN PATENT DOCUMENTS

| WO | WO 2000/26401 | 5/2000 |
|---|---|---|
| WO | WO 2000/70090 | 11/2000 |
| WO | WO 2001/77377 | 4/2001 |
| WO | WO 2002/00927 | 7/2001 |
| WO | WO 2001/62961 | 8/2001 |
| WO | WO 2002/18649 | 3/2002 |
| WO | WO 2002/083705 | 4/2002 |
| WO | WO2002/034942 | 5/2002 |
| WO | WO 2003/074734 | 9/2003 |
| WO | WO 2004/018497 | 3/2004 |
| WO | WO 2004/050915 | 6/2004 |
| WO | WO 2004/051224 | 6/2004 |
| WO | WO2004/094664 | 11/2004 |
| WO | WO 2004/097003 | 11/2004 |
| WO | WO 2005/068656 | 7/2005 |
| WO | WO 2007/010252 | 1/2007 |
| WO | WO 2007/091077 | 8/2007 |
| WO | WO 2007/135368 | 11/2007 |
| WO | WO 2008/041002 | 4/2008 |
| WO | WO 2008/093098 | 8/2008 |
| WO | WO 2009/032167 | 3/2009 |
| WO | WO 2009/120372 | 10/2009 |
| WO | WO 2009/132315 | 10/2009 |

OTHER PUBLICATIONS

Costello, J F., "Methylation Matters", Journal of Medical Genetics, London, Great Britain.vol. 38., No. 5., May 2001 p. 285-303, XP008018005, 285-303.

Dahl, et al., "DNA methylation analysis techniques", Biogerontology, 4 (4):233-250 (2003), 2003, 233-250.

Draper, "Attachment of reporter groups to be specific, selected cytidine residues in RNA using a bisulfite-catalyzed transamination reaction", Nucleic Acid Research, vol. 12, Jan. 1984.

Eads, "CpG island hypermethylation in human colorectal tumors is not associated with DNA methyltransferase overexpression", Cancer Res. 59 (10):2302-2306 (1999), 1999, 2302-2306.

Eads, et al., "Methylight: a high-throughput assay to measure DNA methylation", Nucleic Acids Research, 28(8), e32, 2000, i-viii.

Esteller, "CpG island methylation and tumor suppressor genes: a booming present, a brighter future", Oncogene 21 (35):5427-40 (2002)., 2002, 5427-40.

Feil, et al., "Methylation analysis on individual chromosomes: improved protocol for bisuphphite genomic sequencing", Nucleic Acids Res. 22 (4 ):695-696 (1994 ), 1994, 695-696.

Feinberg, et al., "Hypomethylation distinguishes genes of some human cancers from their normal counterparts", Nature. 301 (5895):89-92 (1983), 1983, 89-92.

Frommer, et al., "A genomic sequencing protocol that yields a positive display of 5-methylcytosine residues in individual DNA strands", Proc Natl Acad Sci USA, 89 (5):1827-1831 (1992), 1992, 1827-1831.

Gonzalgo, et al., "Identification and characterization of differentially methylated regions of genomic DNA by methylation-sensitive arbitrarily primed PCR", Cancer Res. 57 (4): 594-599 (1997), 1997, 594-599.

Gonzalgo, et al., "Rapid quantitation of methylation differences at specific sites using methylation-sensitive single nucleotide primer extension (Ms-SNuPE)", Nucleic Acids Res. 25 (12):2529-2531 (1997), 1997, 2529-2531.

Gonzalgo, M. et al., "Quantitative methylation anaylsis using methylation sensitive single nucleotide primer extension (Ms-SNuPE)", Methods, 27:128-133 (2002).

Goto, , "Regulation of X-chromosome inactivation in development in mice and humans", Microbial. Mol. Biol. Rev. 62, 1998, 362-378.

Hammons, et al., "Specific site methylation in the f-flanking region of CYP1AS:interindividual differences in human livers", Life Sci 69:839-845 (2001 ), 839-845.

Hanada, et al., "Bc1-2-gene hypomethylation and high-level expression in B-cell chronic lymphocytic leukemia", Blood. 82 (6):1820-1828 (1993), 1993, 1820-1828.

Heid, et al., "Real time quantitative PCR", Genomic Res 6 (10):986-994 (1996), 1996, 986-994.

Herman, et al., "Inactivation of the CDKN2/p16/MTS1 gene is frequently associated with abberrant DNA methylation in all common human cancers", Cancer Res. 55 (20):4525-30 (1995), 1995, 4525-30.

Herman, et al., "Methylation-specific PCR: a novel PCR assay for methylation status of CpG islands", Proc Natl Acad Sci USA 93 (19):9821-9826 (1996), 1996, 9821-9826.

Hermanson, "Bioconjugate Techniques", San Diego Academic Press, 1996, 640-643.

Huang, et al., "Methylation profiling of CpG islands in human breast cancer cells.", Hum Mol Genet. 8 (3):459-470 (1990), 1999, 459-470.

Issa, et al., "Methylation of the oestrogen receptor CpG islands ageing and nepplasia in human colon", Nat Genet. 7 (4) 536-540 (1994 )., 1994, 536-540.

Jones, D H. , "A iterative and regenerative method for DNA sequencing", Biotechniques. vol. 22:939 (1997)., 1997, 939.

Jones, et al., "Cancer epigenetics comes of age", Nature Genetics, 21(2), 1999, 163-1.

Kalisch, et al., "Covalent Linked Sequencing Primer Linkers (Splinkers) for Sequence Analysis of Restriction Fragments", Gene, 44, Department of Medical Biochemistry, Faculty of Medicine, University of Calgary, Calgary, Alberta, 1986, 263-270.

Kaur, "Novel amplification of DNA in a hairpin structure towards a radical elimination of PCR errors from amplified DNA", Nucleic Acid Research, vol. 13, Dec. 2003.

Kawai, et al., "Comparison DNA methylation pattens among cell lines byrestriction landmark genomic scanning", Mol Cell Biol.14 (11 ):7421-7427 (1994), 1994, 7421-7427.

Kozekov, "DNA Interchain Cross-Links Formed by Acrolein and Crotonaldehyde", J Am Chem Soc., Apr. 2002.

Kumar, "Rett and ICF syndromes: methylation moves into medicine", J. Biosci., 25(3 ), 2000, 213-214.

Laird, Charles D. et al., "Hairpin-bisulfite PCR: Assessing epigenetic methylation patterns on comoplementary strands of individual DNA molecules", Proceedings of the national academy of sciences, National Academy of Sciences, vol. 101, No. 1, Jan. 6, 2004, 204-209.

Lewin, et al., "The Mystique of Epigenetics", Cell 93:301-303 (1998), 1998, 301-303.

Marguiles, et al., "Genome Sequencing in Open Microfabricated High Density Picoliter Reactors", Nature, Jul. 2005.

Marguiles, et al., "Library Preparation (Supplementary Figure 1)", Nature, Jul. 2005.

Margulies, et al., "Genome sequencing in microfabricated highdensity picolitre reactors", Nature, vol. 437, 15, Sep. 2005, 376-380.

Nishiyama, et al., "Both Hypomethylation and Hypermethylation in a 0 2-kb Region of a DNA Repeat in Cancer", Mol Cancer Res, Nov. 2005.

Notice of Opposition, "EP Application No. 09822662.4", dated Jun. 30, 2015.

Oakeley, "DNA methylation analysis: A review of current methodologies.", Pharm Thera 84: 389-400 (1999)., Sometimes mistaken for "Costello" with same citation, 1999, 389-400.

Olek et al. "A modified and improved method for bisulphite basedcytosine methylation analysis", Nucl. Acids Res. 24:5064-6, 1996.

Otterson, et al., "CDKN2 gene silencing in lung cancer by DNA hypermethylation and kinetics of p161NK4 protein induction by 5-aza 2'deoxycytidine", Oncogene 11(6):1211-6 (1995), 1995, 1211-1216.

Razin, et al., "CpG methylation, chromatin structure and gene silencing—a three-way connection", EMBO J., 17(17), 1998, 4905-4908.

Razin, et al., "DNA Methylation and embryogenesis", DNA Methylation: Molecular Biology and Biological Significance, 1993, 343-357.

Reik, et al., "Epigenetic reporgramming in mammalian development", Science, 293, 2001, 1089-1093.

(56) References Cited

OTHER PUBLICATIONS

Rein, et al., "Identifying 5-methylcytosine and related modifications in DNA genomes", Nucleic Acids Res. 26 (10):2255-2264 (1998), 1998, 2255-2264.
Reinder, et al., "Genome-wide, high-resolution DNA methylation profiling using bisulfite-mediated cytosine conversion", Genome Research., vol. 18, No. 3, Mar. 2008, 469-476.
Sasaki, et al., "DNA methylation and genomic imprinting in mammals", Exs. 64, 1993, 469-486.
Schulz, "DNA methylation in urological malignancies (review)", Int. J. Oncol. 13, 1998, 151-167.
Singer-Sam, et al., "A quantitative HpaII-PCR assay to measure methylation of DNA from a small number of cells", Nucleic Acids Research, vol. 18, Feb. 1990.
Taylor, et al., "The diagnostic significance of Myf-3 hypermethylation in malignant limphoproliferative disorders", Leukemia 15(4):583-589 (2001), 2001, 583-589.
Toyota, et al., "Identification of differentially methylated sequences in colorectal cancer by methylated CpG island amplification", Cancer Res. 59 (10):2307-2312 (1999), 1999, 2307-2312.
Trinh, et al., "DNA Methylation Analysis by Methylight Technology", Methods, 25, 2001, 456-462.
Wong, et al., "PCR with 5-methyl-dCTP replacing dCTP", Nucleic Acid Research, vol., Mar. 19, 1991.
Yan, et al., "CpG island Arrays: An application toward deciphering epigenetic signatures of breast cancer", Clin. Cancer Res. 6:1432-1438 (2000), 2000, 1432-1438.
Yan, et al., "Role of DNA methylation and histone acetylation in steroid receptor expression in breast cancer", J. Mammary Gland Biol. Neoplasia, 6(2), 2001, 183-192.
Zhou, "Universal TA Cloning", Curr Issues Mol Biol, 2000.

\* cited by examiner

PRESERVATION OF INFORMATION RELATED TO GENOMIC DNA METHYLATION

CROSS-REFERENCE TO RELATED APPLICATIONS

This application is a division of U.S. application Ser. No. 14/327,892, filed on Jul. 10, 2014 which is a continuation of U.S. application Ser. No. 14/020,241, filed on Sep. 6, 2013, now U.S. Pat. No. 8,895,268, issued on Nov. 25, 2014 which is a division of U.S. application Ser. No. 13/125,419, filed on Apr. 21, 2011, now U.S. Pat. No. 8,541,207, issued on Sep. 24, 2013 which is the U.S. National Stage Entry of Int. App. No. PCT/US09/61552, filed Oct. 21, 2009 which claims priority to U.S. Prov. App. No. 61/107,457, filed on Oct. 22, 2008, each of which is incorporated herein by reference in its entirety.

BACKGROUND OF THE INVENTION

Field of the Invention

The present invention relates to the fields of biology and genomics. More specifically, the present invention relates to compositions, methods and systems for analyzing the methylation state of nucleic acids.

Description of the Related Art

Biomolecule methylation, such as DNA methylation is widespread and plays a critical role in the regulation of gene expression in development, differentiation and disease. Methylation in particular regions of genes, for example their promoter regions, can inhibit the expression of these genes. Recent work has shown that the gene silencing effect of methylated regions is accomplished through the interaction of methylcytosine binding proteins with other structural components of the chromatin, which, in turn, makes the DNA inaccessible to transcription factors through histone deacetylation and chromatin structure changes. Genomic imprinting in which imprinted genes are preferentially expressed from either the maternal or paternal allele also involves DNA methylation. Deregulation of imprinting has been implicated in several developmental disorders.

In vertebrates, the DNA methylation pattern is established early in embryonic development and in general the distribution of 5-methylcytosine (5mC) along the chromosome is maintained during the life span of the organism. Stable transcriptional silencing is critical for normal development, and is associated with several epigenetic modifications. If methylation patterns are not properly established or maintained, various disorders like mental retardation, immune deficiency and sporadic or inherited cancers may follow. The study of methylation is particularly pertinent to cancer research as molecular alterations during malignancy may result from a local hypermethylation of tumor suppressor genes, along with a genome wide demethylation.

The initiation and the maintenance of the inactive X-chromosome in female eutherians were found to depend on methylation. Rett syndrome (RTT) is an X-linked dominant disease caused by mutation of MeCP2 gene, which is further complicated by X-chromosome inactivation (XCI) pattern. The current model predicts that MeCP2 represses transcription by binding methylated CpG residues and mediating chromatin remodeling.

DNA methylation pattern changes at certain genes often alter their expression, which could lead to cancer metastasis, for example. Thus, studies of methylation pattern in selected, staged tumor samples compared to matched normal tissues from the same patient offers a novel approach to identify unique molecular markers for cancer classification. Monitoring global changes in methylation pattern has been applied to molecular classification in breast cancer. In addition, many studies have identified a few specific methylation patterns in tumor suppressor genes (for example, p16, a cyclin-dependent kinase inhibitor) in certain human cancer types.

Restriction landmark genomic scanning (RLGS) profiling of methylation pattern of 1184 CpG islands in 98 primary human tumors revealed that the total number of methylated sites is variable between and in some cases within different tumor types, suggesting there may be methylation subtypes within tumors having similar histology. Aberrant methylation of a proportion of these genes correlates with loss of gene expression.

Since genomic DNA is often the target of methylation analyses, it offers advantages in both the availability of the source materials and ease of performing such analyses. Also, methylation analyses of genomic DNA can be complementary to those used for RNA-based gene expression profiling.

Accordingly, there is a need for improved methods of determining the methylation status of DNA. The compositions, methods and systems described herein satisfy this need and provide other advantages as well.

SUMMARY OF THE INVENTION

A method of sequencing nucleic acid comprising cytosine is provided. The method can include the steps of providing a sample comprising a template nucleic acid; generating a complementary copy of the template nucleic acid, wherein the generating produces a complementary copy of the template nucleic acid such that cytosine residues in the complementary copy are conversion resistant cytosine analogs comprising a moiety that inhibits conversion to another base residue; subjecting the template nucleic acid and the complementary copy to conversion treatment to convert cytosine residues in the template nucleic acid into residues comprising the other base, resulting in a converted template nucleic acid and a non-converted complementary copy; and determining the nucleotide sequence of the converted template nucleic acid and the non-converted complementary copy. In certain aspects, the generating is directed by an oligonucleotide primer using a nucleic acid polymerase in the presence of a cytosine analog that comprises a moiety that inhibits conversion to the other base residue. In certain aspects, the method further comprises comparing the nucleotide sequence of the non-converted complementary copy to the nucleotide sequence of the converted template nucleic acid, thereby obtaining the nucleotide sequence of the template prior to conversion.

A method of sequencing nucleic acid comprising deaminated cytosine is provided. The method can include the steps of providing a sample comprising a template nucleic acid; generating a complementary copy of the template nucleic acid, the generating being directed by an oligonucleotide primer using a nucleic acid polymerase in the presence of a bisulfite-resistant cytosine analog, wherein the generating produces a complementary copy of the template nucleic acid such that cytosine residues in the complementary copy are methylated; subjecting the template nucleic acid and the complementary copy to bisulfite treatment to convert unmethylated cytosine residues in the template nucleic acid into uracil residues, resulting in a bisulfite-converted template nucleic acid and a non-converted complementary copy; and determining the nucleotide sequence of the bisulfite-converted template nucleic acid and the non-converted complementary copy. In certain aspects, the method further comprises comparing the nucleotide sequence of the non-converted complementary copy to the nucleotide sequence of the bisulfite-converted template nucleic acid, thereby obtaining the nucleotide sequence of the template prior to bisulfite conversion.

A method of identifying methylated cytosines in DNA is also provided. The method can include the steps of obtaining bisulfite-converted template nucleic acid comprising at least one uracil residue; obtaining a non-converted complementary copy of the template nucleic acid; determining the nucleotide sequence of the bisulfite-converted template nucleic acid; determining the nucleotide sequence of the non-converted complementary copy of the template nucleic acid; comparing the nucleotide sequence of the non-converted complementary copy of the template nucleic acid to the bisulfate-converted template nucleic acid, thereby determining the nucleotide sequence and the methylation status of the template nucleic acid prior to bisulfate conversion.

In certain aspects, the method further comprises comparing the nucleotide sequence of the non-converted complementary copy of the template nucleic acid to a sequence in a database. In certain aspects, the method further comprises comparing the nucleotide sequence of the bisulfate-converted template nucleic acid to a sequence in a database.

In certain aspects of the above embodiments, the template nucleic acid is DNA. In certain aspects, the cytosine analog, for example, a bisulfate-resistant cytosine analog, is capable of incorporation into nucleic acid by a nucleic acid polymerase. For example, the bisulfate-resistant cytosine analog can be selected from the group consisting of: 5-ethyl dCTP, 5-methyl dCTP, 5-fluoro dCTP, 5-bromo dCTP, 5-iodo dCTP, 5-chloro dCTP, 5-trifluoromethyl dCTP, 5-aza dCTP, as well as other bisulfate-resistant nucleotides comprising a cytosine analog. In certain aspects, the bisulfate-resistant cytosine analog is 5-methyl dCTP. In certain aspects, the template nucleic acid is double-stranded. In other aspects, the template nucleic acid is single-stranded. In certain aspects, the oligonucleotide primer is capable of forming a hairpin loop. In some aspects, the complementary copy is covalently coupled to the template nucleic acid. In such aspects, the oligonucleotide primer may be ligated to the template nucleic acid prior to the generating step.

In certain aspects, the above methods can further comprise the step of pairing the non-converted complementary copy and said converted template nucleic acid. In certain aspects, pairing is accomplished via a physical tether between the complementary copy and the converted template nucleic acid. In other certain aspects, pairing is accomplished via tag molecules which identify the complementary copy and the converted template nucleic acid as members of a nucleic acid pair.

In some compositions, methods and systems described herein, the oligonucleotide primer comprises sequence complementary to a sequencing primer. In some aspects, a second oligonucleotide primer is ligated to the complementary copy prior to conversion treatment, such as bisulfite conversion. The second oligonucleotide primer can comprise sequence complementary to, for example, a sequencing primer or a capture probe. In some aspects, the oligonucleotide primer is covalently coupled to the complementary copy but not to the template nucleic acid prior to conversion treatment, such as bisulfite conversion. In some such aspects, the template nucleic acid is covalently coupled to a partner oligonucleotide, where the oligonucleotide primer and the partner oligonucleotide comprise a unique tag sufficient to identify the template nucleic acid and the complementary copy.

Also provided herein is a method of identifying methylated cytosines in a plurality of nucleic acids. The method can include the steps of: providing a sample comprising a plurality of template nucleic acids; generating complementary copies of the template nucleic acids, wherein the generating produces a complementary copy of the template nucleic acid such that cytosine residues in the complementary copy are conversion resistant cytosine analogs comprising a moiety that inhibits conversion to an other base residue, and wherein each complementary copy is coupled to one of the template nucleic acids; subjecting the template nucleic acids and the complementary copies to conversion treatment to convert cytosine residues in the template nucleic acids into residues comprising the other base, resulting in each converted template nucleic acid being coupled to a non-converted complementary copy; determining the nucleotide sequence of the converted template nucleic acids and the non-converted complementary copies; and comparing the nucleotide sequence of the converted template nucleic acids to the nucleotide sequence of the non-converted complementary copies for each of the converted template nucleic acids coupled to non-converted complementary copies, thereby determining the methylation status of the template nucleic acids prior to conversion.

In particular embodiments, the method of identifying methylated cytosines in a plurality of nucleic acids can include the steps of: providing a sample comprising a plurality of template nucleic acids; generating complementary copies of the template nucleic acids, the generating being directed by an oligonucleotide primer using a nucleic acid polymerase in the presence of a bisulfite-resistant cytosine analog, wherein the generating produces a complementary copy of each of the template nucleic acids such that cytosine residues in each complementary copy are methylated, and wherein each complementary copy is coupled to one of the template nucleic acids; subjecting the template nucleic acids and the complementary copies to bisulfite treatment to convert unmethylated cytosine residues in the template nucleic acids into uracil residues, resulting in each bisulfite-converted template nucleic acid being coupled to a non-converted complementary copy; determining the nucleotide sequence of the bisulfite-converted template nucleic acids and the non-converted complementary copies; and comparing the nucleotide sequence of the bisulfite-converted template nucleic acids to the nucleotide sequence of the non-converted complementary copies for each of the bisulfite-converted template nucleic acids coupled to non-converted complementary copies, thereby determining the methylation status of the template nucleic acids prior to bisulfite conversion.

In certain aspects of the above embodiment, the plurality of nucleic acids can comprise greater than 10, 100, 1,000, 10,000, 100,000 or greater than 1,000,000 nucleic acids having different sequences. In some embodiments, nucleic acids having the same or similar sequences can be present in the plurality of nucleic acids. In some embodiments, the similar sequences has a single base mismatch. In other embodiments, similar sequences have multiple base mismatches. In certain aspects of the above-described methods, the templates comprise a universal priming site and the same oligonucleotide primer sequence is used to generate complementary copies of the template nucleic acids.

In certain aspects, the template nucleic acids are DNA. In certain aspects, the cytosine analog, for example, a bisulfite-resistant cytosine analog, is capable of incorporation into nucleic acid by a nucleic acid polymerase. In certain aspects, the bisulfite-resistant cytosine analog is selected from the group consisting of: 5-ethyl dCTP, 5-methyl dCTP, 5-fluoro dCTP, 5-bromo dCTP, 5-iodo dCTP, 5-chloro dCTP, 5-trifluoromethyl dCTP, 5-aza dCTP, as well as other bisulfite-resistant nucleotides comprising a cytosine analog. In certain aspects, the bisulfite-resistant cytosine analog is 5-methy dCTP. In certain aspects, the template nucleic acids are double-stranded. In certain aspects, the template nucleic acids are single-stranded.

In certain aspects, the oligonucleotide primer is capable of forming a hairpin loop. In certain aspects, the complementary copies are covalently coupled to the different template nucleic acids. In certain aspects, the oligonucleotide primer is ligated to the template nucleic acid prior to the generating step. In certain aspects, the oligonucleotide primer comprises sequence complementary to a sequencing primer.

In certain aspects, the method further comprises the step of ligating a second oligonucleotide primer to each of the complementary copies prior to conversion treatment. In certain aspects, the second oligonucleotide primer comprises sequence complementary to, for example, a sequencing primer or a capture probe. In certain aspects, each oligonucleotide primer is covalently coupled to each complementary copy prior to conversion treatment, but not to each template nucleic acids. In certain aspects, each template nucleic acid is covalently coupled to a partner oligonucleotide, the oligonucleotide primer and the partner oligonucleotide comprising a unique tag sufficient to identify each template nucleic acid and each complementary copy.

In certain aspects, the method further comprises the step of pairing each of the non-converted complementary copies with its corresponding converted template nucleic acid. In certain aspects, the pairing is accomplished via a physical tether between each complementary copy and each corresponding converted template nucleic acid. In certain aspects, the pairing is accomplished via tag molecules which identify each complementary copy and each corresponding converted template nucleic acid as members of a nucleic acid pair.

Also provided herein is a nucleic acid pair and vectors comprising the same. One embodiment is a nucleic acid pair comprising a template nucleic acid comprising a cytosine residue; a complementary copy of the template nucleic acid having every or nearly every cytosine methylated; and a tag capable of identifying the template nucleic acid and the complementary copy of the template nucleic acid as members of the nucleic acid pair, wherein the template nucleic acid and the complementary copy of the template nucleic acid are coupled to the tag.

In certain aspects, the template nucleic acid is DNA. In certain aspects, the template nucleic acid is single-stranded. In certain aspects, the template nucleic acid is single-stranded and the complementary copy is single-stranded. In certain aspects, the bisulfate-resistant cytosine analog is selected from the group consisting of: 5-ethyl dCTP, 5-methyl dCTP, 5-fluoro dCTP, 5-bromo dCTP, 5-iodo dCTP, 5-chloro dCTP, 5-trifluoromethyl dCTP, 5-aza dCTP, as well as other bisulfate-resistant nucleotides comprising a cytosine analog. In certain aspects, the bisulfate-resistant cytosine analog is 5-methyl dCTP.

In certain aspects, the tag is a molecule disposed between the template nucleic acid and the complementary copy. In certain aspects, the molecule comprises an oligonucleotide comprising a hairpin loop. In certain aspects, the tag comprises a first and second oligonucleotide comprising an identical nucleotide sequence, wherein the first oligonucleotide is coupled to the template nucleic acid and the second oligonucleotide is coupled to the complementary copy. In certain aspects, the tag comprises a first and second oligonucleotide comprising complementary nucleotide sequence, wherein the first oligonucleotide is coupled to the template nucleic acid and the second oligonucleotide is coupled to the complementary copy.

Another embodiment is a population of different nucleic acid pairs. The population can comprise: template nucleic acids and complementary copies of the template nucleic acids attached to each other as covalent pairs via a nucleic acid loop, wherein the template nucleic acids each comprise at least one cytosine residue, wherein every cytosine of the complementary copies replaced by a conversion-resistant cytosine analog; and wherein different nucleic acid pairs in the population have different sequences for the template nucleic acids and the same sequence for the nucleic acid loop.

In certain aspects, the template nucleic acids are DNA. In certain aspects, the template nucleic acids are single-stranded. In certain aspects, the template nucleic acids are single-stranded and the complementary copies are single-stranded. In certain aspects, the bisulfate-resistant cytosine analog is selected from the group consisting of: 5-ethyl cytosine, 5-methyl cytosine, 5-fluoro cytosine, 5-bromo cytosine, 5-iodo cytosine, 5-chloro cytosine, 5-trifluoromethyl cytosine, 5-aza cytosine as well as other bisulfate-resistant nucleotides comprising a cytosine analog. In certain aspects, the bisulfate-resistant cytosine analog is 5-methyl cytosine.

Also presented herein is a method of making an array, comprising the steps of providing the population of nucleic acid pairs as described hereinabove; providing a solid support with a plurality of sites; and coupling the different pairs from the population to the sites, thereby spatially resolving the different pairs from each other.

A method of making an array is also provided. The method can include the steps of: providing a sample comprising a template nucleic acid; generating a complementary copy of the template nucleic acid, wherein the generating produces a complementary copy of the template nucleic acid such that cytosine residues in the complementary copy are conversion resistant cytosine analogs comprising a moiety that inhibits conversion to an other base residue; subjecting the template nucleic acid and the complementary copy to conversion treatment to convert cytosine residues in the template nucleic acid into residues comprising the other base, resulting in a converted template nucleic acid and a non-converted complementary copy; and coupling the template and the complementary copy of the template to the solid support.

The method of making an array can include the steps of: providing a solid support with a plurality of sites; providing a sample comprising a template nucleic acid; generating a complementary copy of the template nucleic acid, the generating being directed by an oligonucleotide primer using a nucleic acid polymerase in the presence of a bisulfite-resistant cytosine analog, wherein the generating produces a complementary copy of the template nucleic acid such that each cytosine residue in the complementary copy is methylated; subjecting the template nucleic acid and the complementary copy to bisulfate treatment to convert unmethylated cytosine residues in the template nucleic acid into uracil residues, resulting in a bisulfate-converted template nucleic acid and a non-converted complementary copy; and coupling the template and the complementary copy of the template to the solid support. In certain aspects of the method, at least one of the sites comprises a capture probe. In certain aspects, the capture probe comprises a nucleotide sequence complementary to the template or a nucleotide sequence complementary to a complementary copy of the template. In other aspects, an oligonucleotide complementary to the capture probe is attached to the template or complementary copy of the template.

In certain embodiments of the above method, the template nucleic acid is DNA. In certain aspects, the conversion-resistant cytosine analog is capable of incorporation into nucleic acid by a nucleic acid polymerase. For example, the conversion-resistant cytosine analog can be a bisulfate-resistant cytosine analog and can be selected from the group consisting of: 5-ethyl dCTP, 5-methyl dCTP, 5-fluoro dCTP, 5-bromo dCTP, 5-iodo dCTP, 5-chloro dCTP, 5-trifluoromethyl dCTP, 5-aza dCTP, as well as other bisulfate-resistant nucleotides comprising a cytosine analog. In certain aspects, the bisulfate-resistant cytosine analog is 5-methyl dCTP. In certain aspects, the template nucleic acid is double-stranded. In other aspects, the template nucleic acid is single-stranded. In certain aspects, the oligonucleotide primer is capable of forming a hairpin loop. In some aspects, the complementary copy is covalently coupled to the template nucleic acid. In such aspects, the oligonucleotide primer may be ligated to the template nucleic acid prior to the generating step.

Further, in some aspects, the oligonucleotide primer comprises sequence complementary to a sequencing primer. In some aspects, the method further comprises the step of ligating a second oligonucleotide primer to the complementary copy prior to conversion treatment. In certain aspects, the second oligonucleotide primer comprises sequence complementary to a sequencing primer. In certain aspects, the second oligonucleotide primer comprises sequence complementary to a capture probe. In certain aspects, the oligonucleotide primer is covalently coupled to the complementary copy prior to conversion treatment, but not to the template nucleic acid. In certain such aspects, the template nucleic acid is covalently coupled to a partner oligonucleotide, the oligonucleotide primer and the partner oligonucleotide comprising a unique tag sufficient to identify the template nucleic acid and the complementary copy.

Some compositions described herein relate to an array comprising: a solid support with a plurality of sites, a converted template nucleic acid; and a non-converted complementary copy of the template nucleic acid; wherein the converted template nucleic acid is coupled to at least one of the plurality of sites and the non-converted complementary copy is coupled to at least one of the plurality of sites. In some aspects, the converted template nucleic acid and the non-converted complementary copy are annealed to the same site. In certain aspects, the converted template nucleic acid is annealed to at least one of the plurality of sites and the non-converted complementary copy is annealed to at least one of the plurality of sites. In other aspects, each cytosine residue is replaced by a conversion resistant cytosine analog comprising a moiety that inhibits conversion to an other base residue in the non-converted complementary copy of the template nucleic acid. In particular embodiments, the converted template nucleic acid is a bisulfate-converted template nucleic acid and the conversion resistant cytosine analog is a boisulfite-resistant cytosine analog. For example, the bisulfate-resistant cytosine analog can be selected from the group consisting of: 5-ethyl cytosine, 5-methyl cytosine, 5-fluoro cytosine, 5-bromo cytosine, 5-iodo cytosine, 5-chloro cytosine, 5-trifluoromethyl cytosine, 5-aza cytosine, as well as other bisulfate-resistant nucleotides comprising a cytosine analog. In certain aspects, the bisulfate-resistant cytosine analog is 5-methyl cytosine. In certain aspects, each unmethylated cytosine residue in the bisulfate-converted template nucleic acid has been converted into a uracil residue.

In still other aspects described herein, at least one of the sites comprises a capture probe. In certain aspects, the capture probe comprises a nucleotide sequence complementary to the template nucleic acid or a nucleotide sequence complementary to the complementary copy of the template nucleic acid. In certain aspects, an oligonucleotide complementary to the capture probe is attached to the template or complementary copy of the template.

In some of the above-described embodiments, the complementary copy is covalently coupled to the template nucleic acid. In such aspects, a molecule can be disposed between the template nucleic acid and the complementary copy of the template nucleic acid. In certain aspects, the molecule is an intervening oligonucleotide. In some aspects, the intervening oligonucleotide is capable of forming a hairpin loop. In certain aspects, the intervening oligonucleotide comprises sequence complementary to a sequencing primer. In certain aspects, an additional oligonucleotide is covalently coupled to the complementary copy. The additional oligonucleotide can comprise sequence complementary to a sequencing primer, or to a capture probe, for example.

In other embodiments, a method of identifying methylated cytosines in a nucleic acid is also provided. The method can include the steps of obtaining a template nucleic acid comprising at least a first methyl CpG dinucleotide, obtaining a complementary copy of the template nucleic acid, wherein the complementary copy comprises a complementary methyl CpG dinucleotide in a position opposite the first methyl CpG dinucleotide, subjecting the template nucleic acid and the complementary copy to bisulfite treatment to convert unmethylated cytosine residues in the template nucleic acid into uracil residues, resulting in a bisulfite-converted template nucleic acid and a bisulfite-converted converted complementary copy; determining the nucleotide sequence of the bisulfite-converted template nucleic acid; determining the nucleotide sequence of the bisulfite-converted complementary copy; and comparing the nucleotide sequence of the bisulfite-converted complementary copy to the nucleotide sequence of the bisulfite-converted template nucleic acid, thereby determining the nucleotide sequence of the template nucleic acid prior to bisulfite conversion and the methylation status of the template nucleic acid prior to bisulfite conversion.

In certain aspects of the above embodiment, the method further comprises pairing the bisulfite-converted complementary copy and the bisulfite-converted template nucleic acid. In certain aspects, the pairing is accomplished via a physical tether between the complementary copy and the bisulfite-converted template nucleic acid. In other aspects, the pairing is accomplished via tag molecules which identify the bisulfite-converted complementary copy and the bisulfite-converted template nucleic acid as members of a nucleic acid pair.

In certain embodiments where a physical tether is employed, the physical tether can comprise an oligonucleotide primer capable of forming a hairpin loop. In certain aspects, the oligonucleotide primer is ligated to the template nucleic acid and to the complementary copy prior to the subjecting step. In certain aspects, the oligonucleotide primer can comprise sequence complementary to, for example, a sequencing primer or a capture probe.

In other aspects, the method further comprises the step of ligating a second oligonucleotide primer to the complementary copy or to the template nucleic acid prior to bisulfite treatment. In other aspects, the second oligonucleotide primer comprises sequence complementary to, for example a sequencing primer or a capture probe.

BRIEF DESCRIPTION OF THE DRAWINGS

FIG. 1A shows generation of a complementary copy using a looped oligonucleotide. FIG. 1B shows generation of a complementary copy using an oligonucleotide primer with complementarity to a portion of the template strand.

FIG. 2-2 shows generation of a complementary copy for each of the top and bottom template strands.

FIG. 4A shows alignment of sequences from the same (single-strand) reaction. FIG. 4B shows alignment of sequences from reactions from top and bottom template strands of a double-stranded template nucleic acid.

FIG. 5A shows tags comprising a first and second oligonucleotide comprising identical nucleotide sequences. FIG. 5B shows tags comprising a first and second oligonucleotide comprising complementary nucleotide sequences.

FIG. 6A shows removal of inverted repeat from bisulfate-converted construct in which step (1) depicts 'Copy one of the strands using primer complementary to region A (high primer concentration)'; step (2) depicts 'Perform intermolecular annealing region B and B''; step (3) depicts 'Ligate regions B' and A''; and step (4) depicts 'Break strand next to B (chemical break, sensitive group incorporated in oligo)'. FIG. 6B shows trimming of repeats using a type III restriction endonuclease in which step (5) depicts 'Copy fragment'; step (6) depicts 'Cut with EcoP15I (E denotes EcoP15IU site)'; step (7) depicts 'Ligate EcoP15I site adapters (with 2 base degenerate overhang: 16 possibilities)'; step (8) depicts 'Cut with EcoP15I (E denotes EcoP15IU site)'.

DETAILED DESCRIPTION

Figure 1A:
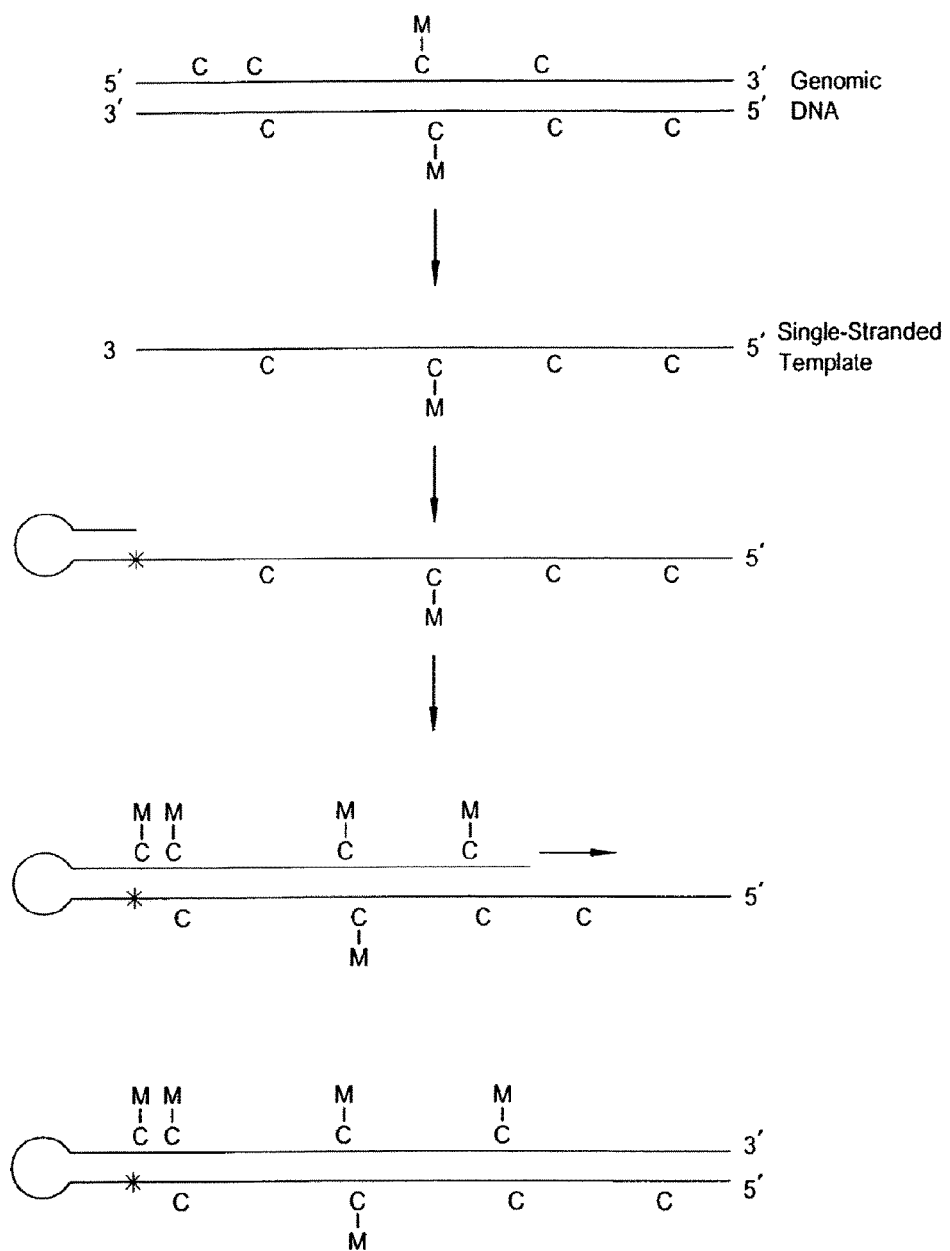
FIGS. 1A-B are schematic drawings of embodiments of a DNA methylation status detection method using a single-stranded template.

The methylation status of nucleic acids is important information that is useful in many biological assays and studies. Very often, it is of particular interest to identify patterns of methylation at specific regions in the genome. Also, it is often of particular interest to identify the methylation status of specific CpG dinucleotides.

The methylation level and pattern of a locus in a nucleic acid sample can be determined using any of a variety of methods capable of distinguishing presence or absence of a methyl group on a nucleotide base of the nucleic acid. In the case of DNA, methylation, when present, typically occurs as 5-methylcytosine (5-mCyt) in CpG dinucleotides. Methylation of CpG dinucleotide sequences or other methylated motifs in DNA can be measured using any of a variety of techniques used in the art for the analysis of specific CpG dinucleotide methylation status.

A commonly-used method of determining the methylation level and/or pattern of DNA requires methylation status-dependent conversion of cytosine in order to distinguish between methylated and non methylated CpG dinucleotide sequences. For example, methylation of CpG dinucleotide sequences can be measured by employing cytosine conversion based technologies, which rely on methylation status-dependent chemical modification of CpG sequences within isolated genomic DNA, or fragments thereof, followed by DNA sequence analysis. Chemical reagents that are able to distinguish between methylated and non methylated CpG dinucleotide sequences include hydrazine, which cleaves the nucleic acid, and bisulfite treatment. Bisulfite treatment followed by alkaline hydrolysis specifically converts non-methylated cytosine to uracil, leaving 5-methylcytosine unmodified as described by Olek A., *Nucleic Acids Res.* 24:5064-6, 1996 or Frommer et al., *Proc. Natl. Acad. Sci. USA* 89:1827-1831 (1992), each of which is incorporated herein by reference in its entirety. The bisulfite-treated DNA can subsequently be analyzed by conventional molecular techniques, such as PCR amplification, sequencing, and detection comprising oligonucleotide hybridization. Several embodiments of the invention are exemplified below by specific reference to use of bisulfite conversion conditions and bisulfite-resistant cytosine analogs. However, the invention need not be limited to the specific conversion methods or conversion-resistant cytosine analogs as these are provided merely as examples to explain aspects of the invention.

One consequence of bisulfite-mediated deamination of cytosine is that the bisulfite treated cytosine is converted to uracil, which reduces the complexity of the genome. Specifically, a typical 4-base genome (A,T,C,G) is essentially reduced to a 3-base genome (A,T,G) because uracil is read as thymine during downstream analysis techniques such as PCR and sequencing reactions. Thus, the only cytosines present are those that were methylated prior to bisulfite conversion. Because the complexity of the genome is reduced, standard methods for comparing and/or aligning a bisulfite-converted sequence to the pre-conversion genome can be cumbersome and in some cases ineffective. For example, problems may arise when aligning converted fragments to the genome, especially when using short sequences. Accordingly, there remains a need for methods which facilitate identification of the genomic context of bisulfite converted DNA.

Provided herein are methods and compositions that surprisingly ameliorate problems that arise from the reduced genomic complexity after bisulfite conversion of nucleic acids. For example, some embodiments described herein relate to methods of sequencing nucleic acids and determining the methylation level and/or pattern of the nucleic acids. Other embodiments relate to nucleic acid pairs, arrays and methods of making arrays useful for determining the methylation level and/or pattern of nucleic acids. Using the methods and/or compositions described herein, complexity of the target nucleic acids is preserved by keeping track of complementary strands after the strands have been subjected to bisulfite conversion of nucleic acids.

In order to preserve complexity of the nucleic acid, some embodiments of the present invention relate to a pairing of the bisulfite-converted sequences of both strands of a double-stranded nucleic acid and using the sequence information from both strands to determine the sequence and/or methylation status of one or both strands prior to bisulfite conversion.

Other embodiments of the present invention relate to making methylated copies of the target nucleic acids prior to bisulfite conversion. The methylated copies can then be sequenced and compared or aligned to the converted target nucleic acids. The methods provided herein are particularly useful in multiplex formats wherein several nucleic acids having different sequences and/or different methylation patterns are assayed in a common sample or pool. Thus, the methods set forth herein can provide the advantage of avoiding the need for separation of different sequences into separate vessels during one or more steps of a methylation detection assay. For example, as set forth in further detail below in regard to particular embodiments, several pairs of nucleic acids can be treated with bisulfate in a common pool and the differences in methylation status for individual nucleic acids from the pool can then be determined.

Although many of the methods and compositions disclosed herein are exemplified or described in connection with DNA, it will be appreciated that these methods and compositions can be used with or include other nucleic acids. Furthermore, it will be understood that methods and compositions described in the context single nucleic acid molecules can also relate to methods and compositions that include or comprise a plurality of the same, similar and/or different nucleic acids. Such embodiments are often referred to as multiplex embodiments. In these multiplex embodiments, the methods are performed using and the compositions comprise a population of nucleic acids. In some embodiments, the population of nucleic acids may be divided into one or more sub-populations.

Definitions

As used herein, reference to determining the methylation status and like terms refers to at least one or more of the following: 1) determining the level or amount of cytosine methylation in a sample, 2) determining the position of methylated cytosine residues within a sequence, 3) determining the pattern of methylated cytosine in a sequence, and/or 4) determining the whole sequence including the specific position and identity of methylated residues in the context of the sequence.

As used herein, "nucleic acid polymerase" or "polymerase" refers to an enzyme that catalyzes the polymerization of nucleoside triphosphates, and encompasses DNA polymerases, RNA polymerases, reverse transcriptases and the like. Generally, the enzyme will initiate synthesis at the 3'-end of the primer annealed to a template sequence, and will proceed in the 5'-direction along the template, and if possessing a 5' to 3' nuclease activity, it may hydrolyze intervening, annealed probe to release both labeled and unlabeled probe fragments, until synthesis terminates.

As used herein, the term "DNA polymerase" refers to an enzyme which catalyzes the synthesis of DNA. It uses a one strand of the DNA duplex as a template. For example, templates may include, but are not limited to, single-stranded DNA, partially duplexed DNA and nicked double-stranded DNA. The polymerase can generate a new strand from primers hybridized to the template. As presented herein, an oligonucleotide primer is used which has a free 3'-OH group. The polymerase then copies the template in the 5' to 3' direction provided that sufficient quantities of free nucleotides, such as dATP, dGTP, dCTP, 5-methyl dCTP and dTTP are present. Examples of DNA polymerases include, but are not limited to, *E. coli* DNA polymerase I, the large proteolytic fragment of *E. coli* DNA polymerase I, commonly known as "Klenow" polymerase, "Taq" polymerase, T7 polymerase, Bst DNA polymerase, T4 polymerase, T5 polymerase, reverse transcriptase, exo-BCA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (PfU) DNA polymerase.

In embodiments of the present invention, the DNA polymerase copies the template in the 5' to 3' direction in the presence of 5-methyl dCTP, or any other suitable nucleotide which is resistant to cytosine conversion such as bisulfite conversion.

As used herein, "converted," when used in reference to a nucleic acid or portion thereof, refers to nucleic acid or a portion thereof which has been treated under conditions sufficient to convert cytosine to another base. As used herein, "bisulfite-converted", "bisulfite-treated" and like terms, when used in reference to a nucleic acid or portion thereof, refer to nucleic acid or a portion thereof which has been treated with sodium bisulfite under conditions sufficient to convert cytosine to uracil. Thus, for example, in some embodiments, template nucleic acid will have at least one cytosine residue that is not methylated and which is converted to uracil by bisulfite treatment. However, the template nucleic acid need not comprise a non-methylated cytosine, either because all cytosines are methylated or because no cytosine residues are present in the template nucleic acid.

As used herein, "non-converted," when used in reference to a nucleic acid or portion thereof, refers to a nucleic acid or portion thereof where one or more of the cytosines, if present, are not converted to another base, such as uracil, after conversion treatment, such as treatment with sodium bisulfite. Thus, for example, a non-converted complementary copy is a nucleic acid that comprises one or more bisulfite-resistant cytosine analogs that prevent the conversion of cytosine to uracil.

As used herein, "conversion-resistant cytosine analog" and like terms refer to cytosine analogs which, when incorporated into DNA, RNA, or other nucleic acid polymers, are refractory to being changed into another base under conditions where cytosine is converted into the other base. As used herein, "bisulfite-resistant cytosine analog" and like terms refer to cytosine analogs which, when incorporated into DNA, RNA, or other nucleic acid polymers, are refractory to deamination caused in reactions with sodium bisulfite. Bisulfite-resistant cytosine analogs are known in the art and can include any cytosine analog with the above-described property. Thus, for example, 5-ethyl dCTP, 5-methyl dCTP, 5-fluoro dCTP, 5-bromo dCTP, 5-iodo dCTP, 5-chloro dCTP, 5-trifluoromethyl dCTP, 5-aza dCTP, or any other bisulfite-resistant nucleotides comprising a cytosine analog can be used in the present embodiments as bisulfite-resistant cytosine analogs. Typically, the bisulfite-resistant cytosine analog is 5-methyl dCTP. Although 5-methyl dCTP and 5-methylcytosine are referred to in the description, examples and figures, it will be readily understood that any suitable bisulfite-resistant cytosine analog can be used in such embodiments.

In some embodiments, "cytosine" refers to nucleotides, nucleosides, nucleotide triphospates and the like which include cytosine (i.e., 4-amino-3H-pyrimidin-2-one) as the base. Thus, for example, where embodiments describe replacing cytosine with a bisulfite-resistant cytosine analog such as 5-methyl cytosine, it will be understood that the term cytosine does not include cytosine residues that are methylated at the 5-position of the cytosine base, unless specifically indicated to the contrary. In some embodiments, the term cytosine can refer to a base structure that is common between cytosine and cytosine analogs, including bisulfite-resistant cytosine analogs, as described in detail herein.

In some embodiments, 5-methyl dCTP replaces all cytosines that complement guanine positions in a complementary copy. In some embodiments, 5-methyl dCTP replaces at least one cytosine that complements a guanine position in the complementary copy. In other embodiments, 5-methyl dCTP replaces at least 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5% or at least 1% of the cytosines that complement guanine positions in the complementary copy. Upon treatment of the complementary copy with sodium bisulfite, those methylated cytosines in the complementary copy are refractory to the deamination reaction, and therefore the genomic complexity is maintained.

As used herein "template nucleic acid" refers to that strand of a polynucleotide from which a complementary polynucleotide strand can be hybridized or synthesized by a nucleic acid polymerase, for example, in a primer extension reaction. In some embodiments, the template nucleic acid is a template DNA.

In embodiments disclosed herein, a template nucleic acid is provided and a complementary copy of the template nucleic acid is generated or provided. The template nucleic acid can be either a single DNA strand or one or both of the single strands in a double-stranded molecule. In embodiments where the template nucleic acid is single stranded, the complementary copy is generated by extending an oligonucleotide primer with a nucleic acid polymerase such that a complementary copy of some or part of the template strand is extended in the 3' direction of the oligonucleotide primer. In a preferred embodiment, the template nucleic acid comprises a template DNA In embodiments where the nucleic acid is double-stranded, one or both strands may serve as the template strand for nucleic acid polymerase. For example, where one strand (the "sense" strand) serves as template, a complementary copy is generated which is complementary to the sense strand. Likewise, where the antisense strand serves as template, a complementary copy is generated which is complementary to the antisense strand. Where both strands serve as template, a separate complementary copy is generated for each of the sense and antisense strands. In a preferred embodiment, each strand of a double-stranded DNA molecule is a template nucleic acid.

As used herein, the term "complementary" refers to nucleic acid sequences that are capable of forming Watson-Crick base-pairs. For example, a complementary sequence of a first sequence is a sequence which is capable of forming Watson-Crick base-pairs with the first sequence. The term "complementary" does not necessarily mean that a sequence is complementary to the full-length of its complementary strand, but the term can mean that the sequence is complementary to a portion thereof. Thus, in some embodiments, complementarity encompasses sequences that are complementary along the entire length of the sequence or a portion thereof. For example, two sequences can be complementary to each other along at least 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or at least 200 consecutive nucleotides. Also, as used herein, a statement that one sequence is complementary to another sequence also encompasses situations in which the two sequences have some mismatches. For example, complementary sequences can include sequences that are complementary along at least 70%, 75%, 80%, 85%, 90%, 91%, 92%, 93%, 94%, 95%, 96%, 97%, 98%, 99%, or 100% of the length of the sequence. Here, the term "sequence" encompasses, but is not limited to, nucleic acid sequences, polynucleotides, oligonucleotides, probes, primers, primer-specific regions, and target-specific regions. Despite the mismatches, the two sequences should have the ability to selectively hybridize to one another under appropriate conditions.

A first nucleic acid strand that is converted, for example using bisulfate treatment, can have conversion induced noncomplementarity with a second strand to which it was previously complementary. For example, cytosines in a first nucleic acid strand may be converted to uracils, such that positions in the first strand that formerly contained cytosines capable of forming Watson-Crick base pairs with guanines at comparable positions in the second, complementary strand are no longer capable of doing so. Nevertheless, for ease of identification, the converted nucleic acid strand may be identified with respect to complementarity of the previous, non-converted first strand to the second strand.

As used herein, the terms "pairing" or "paired" and the like refer to methods used to match a nucleic acid template with its corresponding complementary copy. For example, pairing can be accomplished via a physical tether between the complementary copy and the bisulfate-converted template nucleic acid. Additionally or alternatively, pairing can be accomplished via tag molecules which identify the complementary copy and the bisulfate-converted template nucleic acid as members of a nucleic acid pair. Tag molecules are useful, for example, where the nucleic acid template and the complementary copy are not physically tethered together. Thus, through the use of tag molecules, the two paired members are matched and recognized as members of a pair. The use of covalent tethers and tag molecules are described in further detail below. Also, it will be appreciated that the term "pairing" is not limited to an action or step that must occur at a particular point in the processes described herein. Pairing of nucleic acid sequences can occur at any point in the process that would allow information the information present in a complementary strand to be associated with the information present in a corresponding template strand. As such, when used as a noun, the term "pairing" can refer to any two or more associated nucleic acid strands, whether associated physically or via other methods such as tagging or labeling, that are present at any step of a process described herein or that are present in any of the compositions described herein.

Methods of Sequencing

In accordance with the above, in one embodiment of the present invention, a method of sequencing nucleic acid comprising deaminated cytosine is provided. In a preferred embodiment, the nucleic acid is DNA. In such embodiments, the method can include the steps of providing a sample comprising a template nucleic acid; generating a complementary copy of the template nucleic acid, the generating being directed by an oligonucleotide primer using a nucleic acid polymerase in the presence of a bisulfite-resistant cytosine analog such as 5-methyl dCTP, wherein the generating produces a complementary copy of the template nucleic acid such that cytosine residues in the complementary copy are methylated; subjecting the template nucleic acid and the complementary copy to bisulfite treatment to convert unmethylated cytosine residues in the template nucleic acid into uracil residues, resulting in a bisulfite-converted template nucleic acid and a non-converted complementary copy; and determining the nucleotide sequence of the bisulfite-converted template nucleic acid and the non-converted complementary copy. In certain aspects, the method further comprises comparing the nucleotide sequence of the non-converted complementary copy to the nucleotide sequence of the bisulfite-converted template nucleic acid, thereby obtaining the nucleotide sequence of the template prior to bisulfite conversion.

Further, a method of identifying methylated cytosines in a nucleic acid is also provided. In a preferred embodiment, the nucleic acid is DNA. In such embodiments, the method can include the steps of obtaining bisulfite-converted template nucleic acid comprising at least one uracil residue; obtaining a non-converted complementary copy of the template nucleic acid; determining the nucleotide sequence of the bisulfite-converted template nucleic acid; determining the nucleotide sequence of the non-converted complementary copy of the template nucleic acid; comparing the nucleotide sequence of the non-converted complementary copy of the template nucleic acid to the bisulfite-converted template nucleic acid, thereby determining the nucleotide sequence and/or the methylation status (for example, the level, pattern and/or position of methylated cytosine residues) of the template nucleic acid prior to bisulfite conversion. In certain aspects, the method further comprises comparing the nucleotide sequence of the non-converted complementary copy of the template nucleic acid to a sequence in a database. In certain aspects, the method further comprises comparing the nucleotide sequence of the bisulfite-converted template nucleic acid to the sequence in the database.

In certain aspects of the above embodiments, the template nucleic acid is double-stranded. In other aspects, the template nucleic acid is single-stranded. In certain aspects, the oligonucleotide primer is capable of forming a hairpin loop. In some aspects, the complementary copy is covalently coupled to the template nucleic acid. For example, the oligonucleotide primer can be ligated to the template nucleic acid prior to the generating step.

In some aspects of the methods and compositions described herein, the oligonucleotide primer comprises sequence complementary to a sequencing primer and/or to a capture probe. In some aspects, a second oligonucleotide primer is ligated to the complementary copy prior to bisulfite treatment. Furthermore, the second oligonucleotide primer can comprise sequence complementary to, for example, a sequencing primer or a capture probe. In some aspects, the oligonucleotide primer is covalently coupled to the complementary copy but not to the template nucleic acid prior to bisulfite treatment. As will be discussed in greater detail below, in some aspects, the template nucleic acid is covalently coupled to a partner oligonucleotide, where the oligonucleotide primer and the partner oligonucleotide comprise a unique tag, or at least a sufficiently distinct tag, sufficient to identify the template nucleic acid and the complementary copy.

Figure 1B:
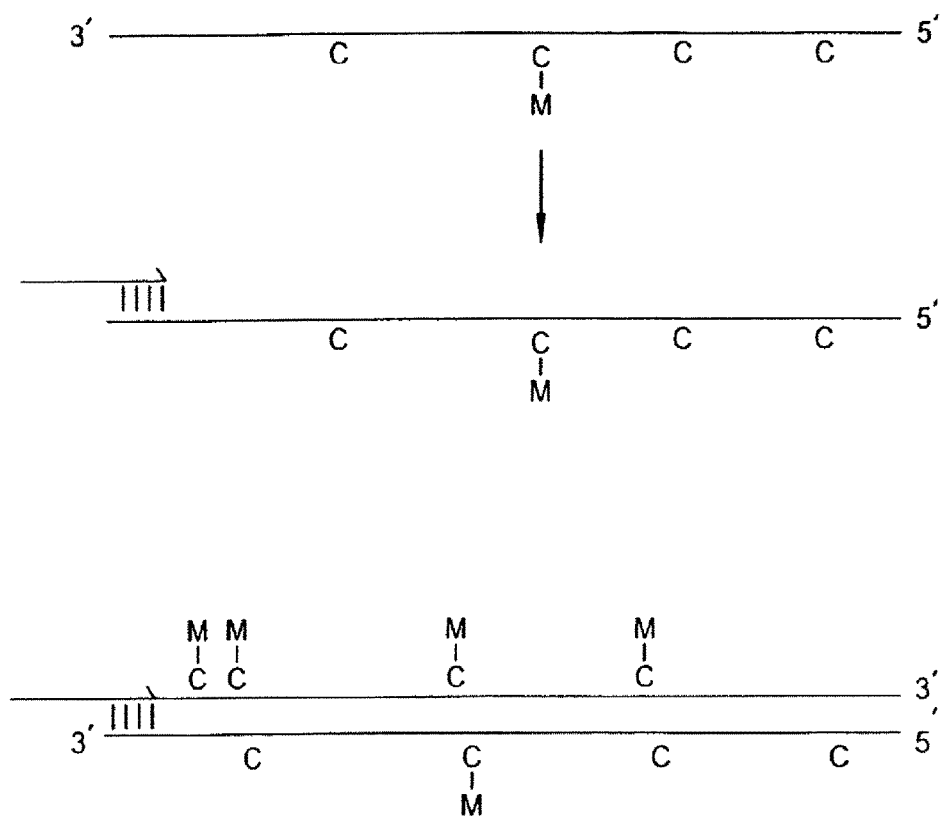
Figure 1:
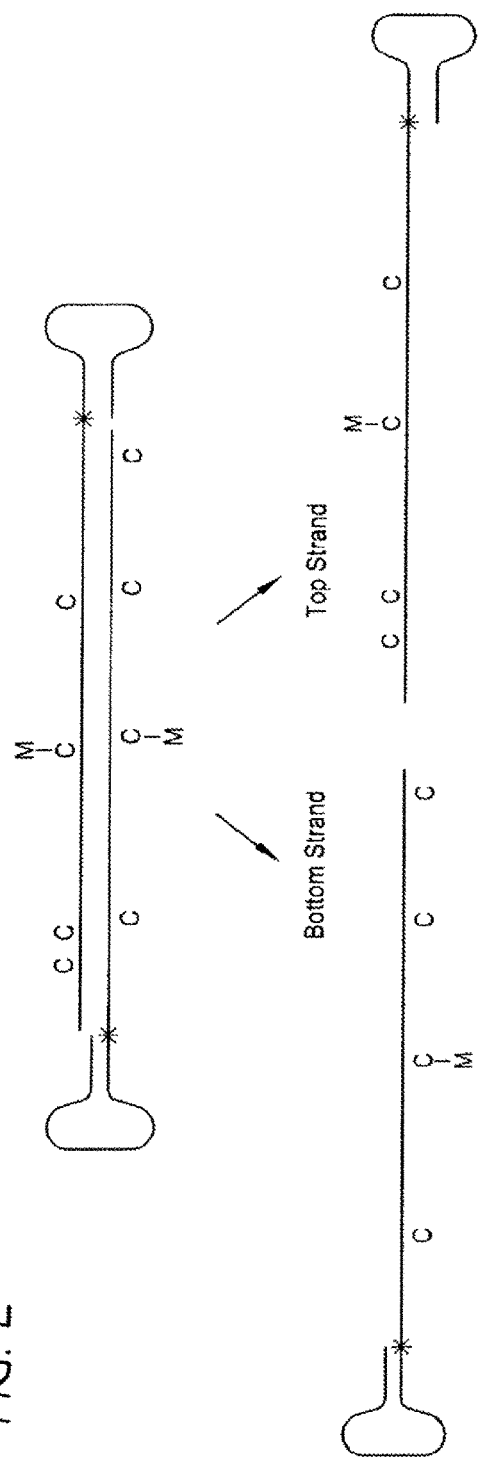
Figure 2:
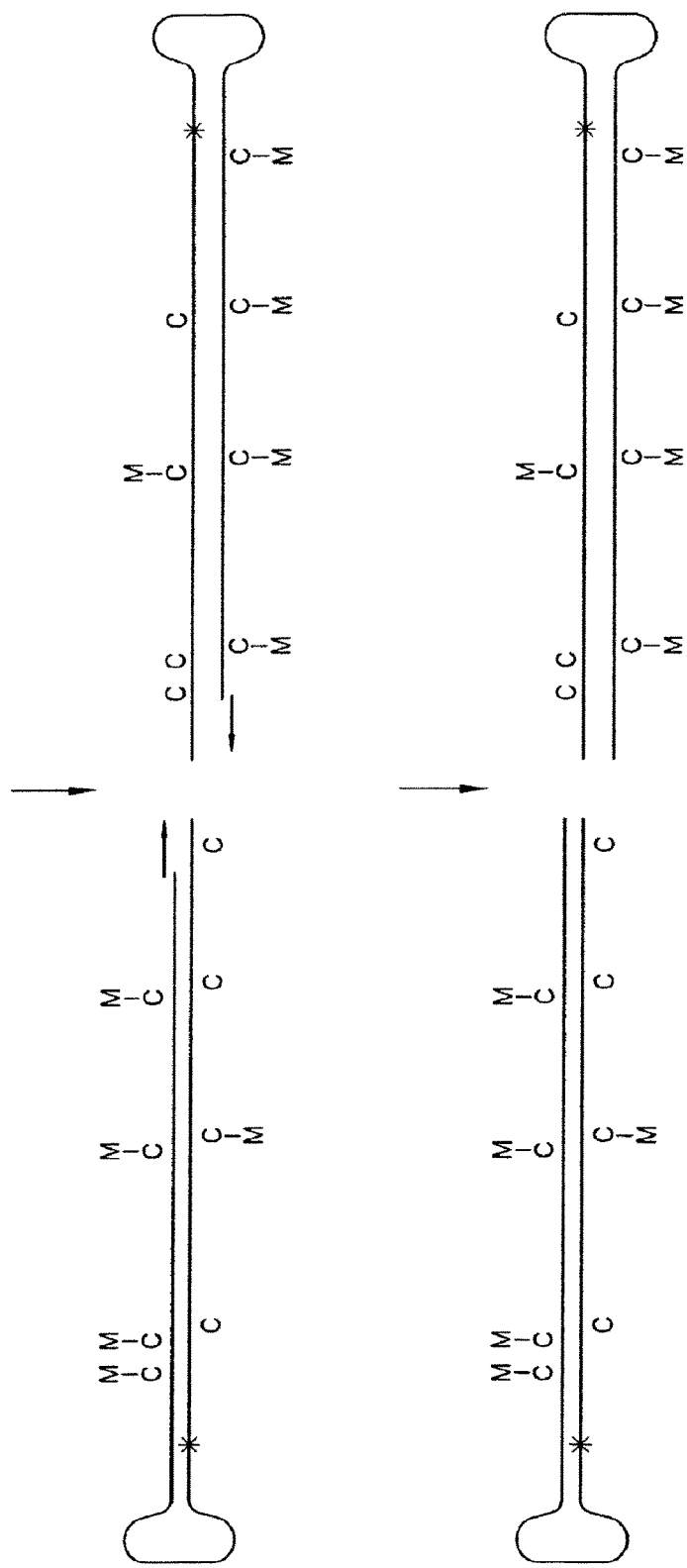

One embodiment of the present invention is set forth in FIG. 1. As shown in FIG. 1A, a single-stranded template is derived from genomic DNA or some other nucleic acid source. Then an oligonucleotide primer, shown here as a looped oligonucleotide, is ligated to the 3' end of the template strand. The looped oligonucleotide has a region of self-complementarity which forms a loop and a stem with a free 3' OH group. A nucleic acid polymerase such as a DNA polymerase is then used to extend the oligonucleotide primer in a 5'→3' direction in the presence of a bisulfite-resistant cytosine analog such as 5-methyl dCTP. The resulting product is a complementary strand that is covalently linked to the template strand via the looped oligonucleotide, forming an (imperfect) inverted repeat. Imperfections in the inverted repeat are due to the incorporation of cytosine analogs in some positions that correspond to positions in the reverse complement having cytosines. Upon bisulfite conversion the positions that are occupied by cytosines will be converted to uracils, whereas positions that are occupied by bisulfite-resistant cytosine will not be converted. Locations occupied by uracil can be considered as imperfections in reference to cytosines at corresponding locations in the reverse complement. One part of the inverted repeat represents the exact genomic sequence, where cytosines are methylated, while the other part is informative in the determination of methylation status. Although the methods are exemplified herein with regard to adding bisulfite-resistant cytosine analogs using a polymerase, it will be understood that such analogs can be added by other methods such as ligation of oligonucleotides having the analogs.

An alternative embodiment is shown in FIG. 1B, where the oligonucleotide primer is not necessarily a looped oligonucleotide. Here, a primer is annealed to the template strand via a region of complementarity. A nucleic acid polymerase is then used to extend the oligonucleotide primer in the presence of a bisulfate-resistant cytosine analog such as 5-methyl dCTP, as described above for the looped oligonucleotide embodiment. One part of the resulting double-stranded product represents the exact genomic sequence, where cytosines are methylated, while the other part is informative in the determination of methylation status.

Figure 2:
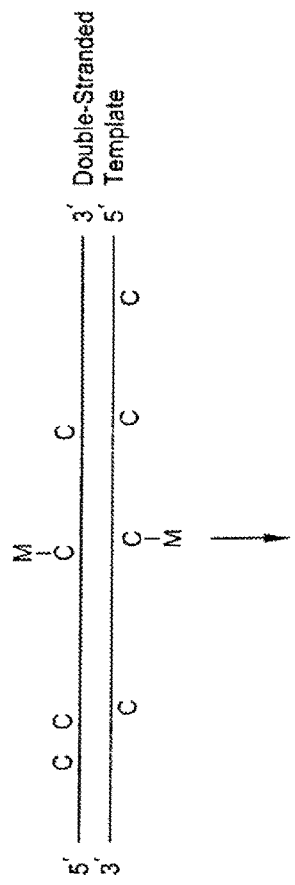
FIG. 2-1 is a schematic drawing showing generation of a complementary copy using a double-stranded template.

In further embodiments of the present invention, complementary copies are generated using a double-stranded template. FIG. 2 represents such an embodiment. Generation of a complementary copy for each of the top and bottom template strands is accomplished via an oligonucleotide primer for each strand. Thus, where the oligonucleotide primer is a looped oligonucleotide, the reactions result in a complementary strand for each of the top and bottom strands. Each complementary strand is covalently linked to its corresponding template strand via the looped oligonucleotide, forming an (imperfect) inverted repeat. One part of the inverted repeat represents the exact genomic sequence, where cytosines are methylated, while the other part is informative in the determination of methylation status. As described above for single-stranded templates, other oligonucleotide primers can be used which are not looped, and one part of each resulting double-stranded product represents the exact genomic sequence, where cytosines are methylated, while the other part is informative in the determination of methylation status.

Figure 3:
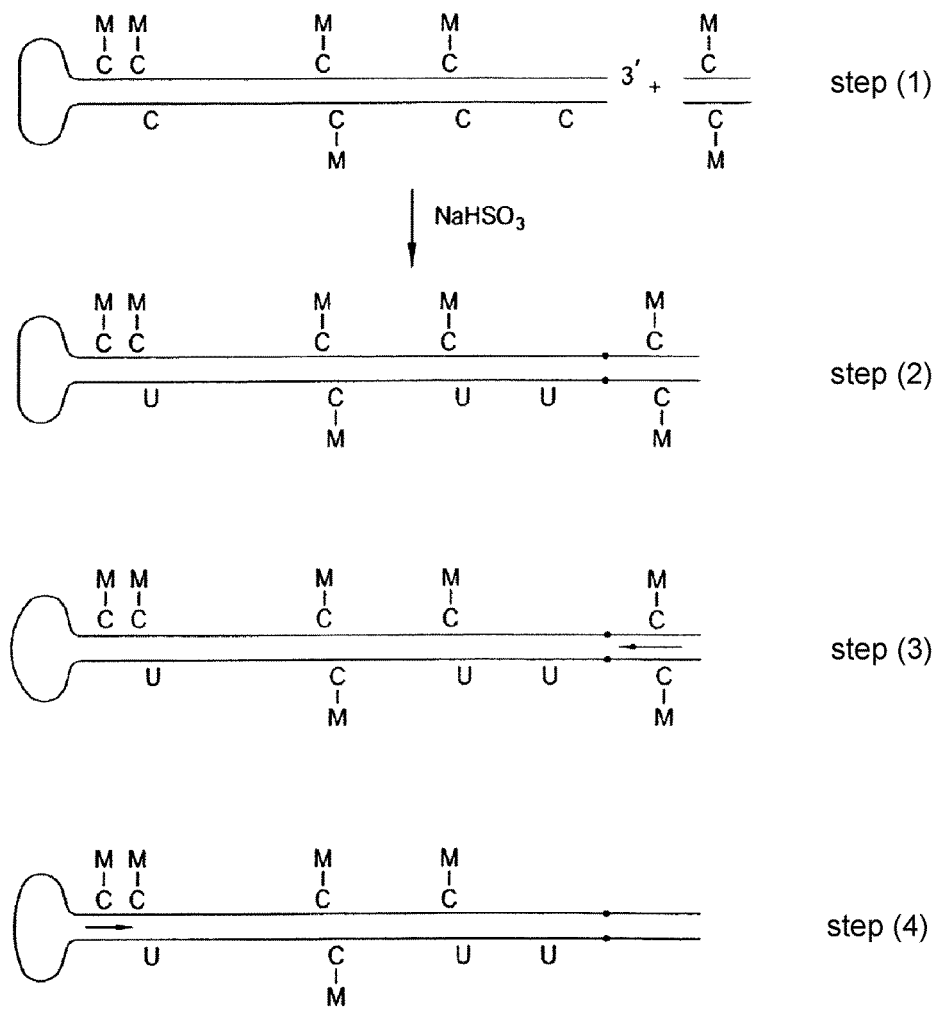
FIG. 3 is a schematic drawing showing bisulfite conversion and sequencing of a methylated complementary copy and of a converted template nucleic acid in which step (1) depicts 'Phosphorylate and Blunt-end Ligation of Sequencing- and/or Capture Probe-Compatible Primer(s)'; step (2) depicts 'Bisulfate Conversion'; step (3) depicts 'Sequence Complementary Copy'; and step (4) depicts 'Sequence Converted Template'.

In order to interrogate the methylation status of the template strand, a cytosine conversion reaction is performed. In some embodiments, such as those depicted in FIG. 3, a second oligonucleotide primer can be first ligated to the 3' end of the complementary copy using techniques known in the art. The second oligonucleotide primer can contain sequence useful for capture on an array, for example, or to facilitate sequencing of the complementary copy. Where bisulfite conversion is used to interrogate the methylation status of the template strand, the complementary copy and the template strand are subjected to bisulfite conversion, as described in further detail below. As a result of bisulfite conversion, unmethylated cytosines in the template nucleic acid are converted to uracil residues, while methylated cytosines are unchanged. In embodiments where the second oligonucleotide comprises sequence that will be used in later steps (i.e., for capture on an array or for binding of a sequencing primer), the second oligonucleotide can be synthesized using a bisulfite-resistant cytosine analog such as 5-methyl dCTP in the positions where maintaining a cytosine at that position is important. For example, as shown in FIG. 3, after bisulfite conversion, a sequencing primer can hybridize to a portion of the second oligonucleotide for use in a sequencing reaction.

Additionally, the oligonucleotide primer (e.g., the looped oligonucleotide primer) can comprise sequence useful in later steps such as capture on an array or for binding of a sequencing primer. Accordingly, as shown in FIG. 3, a sequencing primer can hybridize to a portion of the oligonucleotide primer for use in a sequencing reaction. It will be recognized by those of skill in the art that the oligonucleotide primer can be synthesized using a bisulfite-resistant cytosine analog such as 5-methyl dCTP in the positions where maintaining a cytosine at that position is important in steps that occur subsequent to bisulfite conversion.

Sequence Comparison and Alignment

Some of the embodiments provided herein relate to methods of identifying methylated cytosines in a nucleic acid. In a preferred embodiment, the nucleic acid is DNA. In an exemplary embodiment, the methods comprise the steps of: obtaining bisulfite-converted template nucleic acid which may or may not comprise at least one uracil residue, obtaining a non-converted complementary copy of the template nucleic acid, determining the nucleotide sequence of the bisulfite-converted template nucleic acid; determining the nucleotide sequence of the non-converted complementary copy of the template nucleic acid; and comparing the nucleotide sequence of the non-converted complementary copy of the template nucleic acid to the bisulfite-converted template nucleic acid, thereby determining the nucleotide sequence and/or the methylation status of the template nucleic acid prior to bisulfite conversion.

In certain embodiments, the methods can further comprise the step of comparing the nucleotide sequence of the non-converted complementary copy of the template nucleic acid to a sequence in a database. In certain other embodiments, the method comprises the further step of comparing the nucleotide sequence of the bisulfite-converted template nucleic acid to the sequence in the database.

Thus, in such embodiments, the step of obtaining a non-converted complementary copy of the template nucleic acid can include generating a complementary copy of the template nucleic acid, the generating being directed by an oligonucleotide primer using a nucleic acid polymerase in the presence of a bisulfite-resistant cytosine analog such as 5-methyl dCTP, wherein the generating produces a complementary copy of the template nucleic acid such that cytosine residues in the complementary copy are methylated. The generation of a complementary copy of template nucleic acid is described in further detail hereinabove.

In certain aspects of the above embodiments, the template nucleic acid can be either double-stranded or single-stranded. In certain aspects, the oligonucleotide primer is capable of forming a hairpin loop. In some embodiments, the complementary copy is covalently coupled to the template nucleic acid. For example, the oligonucleotide primer can be ligated to the template nucleic acid prior to the generating step.

In aspects of the above embodiments, the oligonucleotide primer can comprise sequence complementary to a sequencing primer and/or to a capture probe. In certain aspects, the generating step further can comprise the step of ligating a second oligonucleotide primer to the complementary copy prior to bisulfite treatment. The second oligonucleotide primer can also comprise sequence complementary to a sequencing primer. Additionally, such a second oligonucleotide primer can comprise sequence complementary to a capture probe.

In certain aspects of the above embodiment, the oligonucleotide primer is covalently coupled to the complementary copy prior to bisulfite treatment, but not to the template nucleic acid. In such embodiments, the template nucleic acid can be covalently coupled to a partner oligonucleotide, the oligonucleotide primer and the partner oligonucleotide comprising a unique tag, or at least a sufficiently distinct tag, sufficient to identify the template nucleic acid and the complementary copy.

Figure 4A:
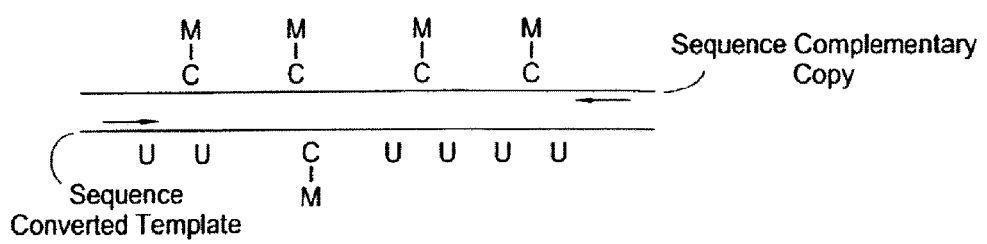
FIGS. 4A-B are schematic drawings showing alignment of sequences obtained from complementary copy and from converted template nucleic acid.
Figure 4A:
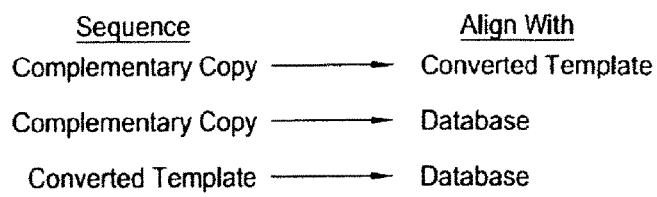

FIG. 4A represents an embodiment where alignment is performed using sequences from a single-stranded reaction. In this embodiment, as set forth in FIG. 4A, the complementary copy generated from one template strand is sequenced. Additionally, the bisulfite-converted template strand may be sequenced. In one aspect of this embodiment, the sequence data obtained for the complementary copy is then aligned with the sequence data obtained for the bisulfate-converted template. Thus, although the converted template strand may contain one or more uracil residues, they are interpreted by sequencing techniques as thymine residues. Thus, alignment of the converted template to the complementary copy provides a reference to identify those thymines which correspond to cytosine in the template nucleic acid prior to bisulfate conversion.

The sequence data of either the complementary copy, or the converted template, or both, may be compared or aligned to sequence data in a database. This is especially useful where there is little or no overlap between the sequence data obtained from the complementary copy and from the converted template. Thus, where sequence data are obtained for only a short region of the complementary copy, the data can be compared or aligned with a larger sequence in a database, in order to find an area of overlap with the sequence data obtained from the converted template.

As shown in FIG. 4A, the sequence data obtained for the complementary copy and the converted template will be complements of each other, with a mismatch in any position where unmethylated cytosine is converted to uracil. Accordingly, in order to align the two sequences in the same orientation, either the sequence data obtained for the complementary copy or for the converted template can be manipulated to obtain the corresponding complement sequence, which then can be aligned in the same orientation with the other sequence obtained.

Figure 4B:
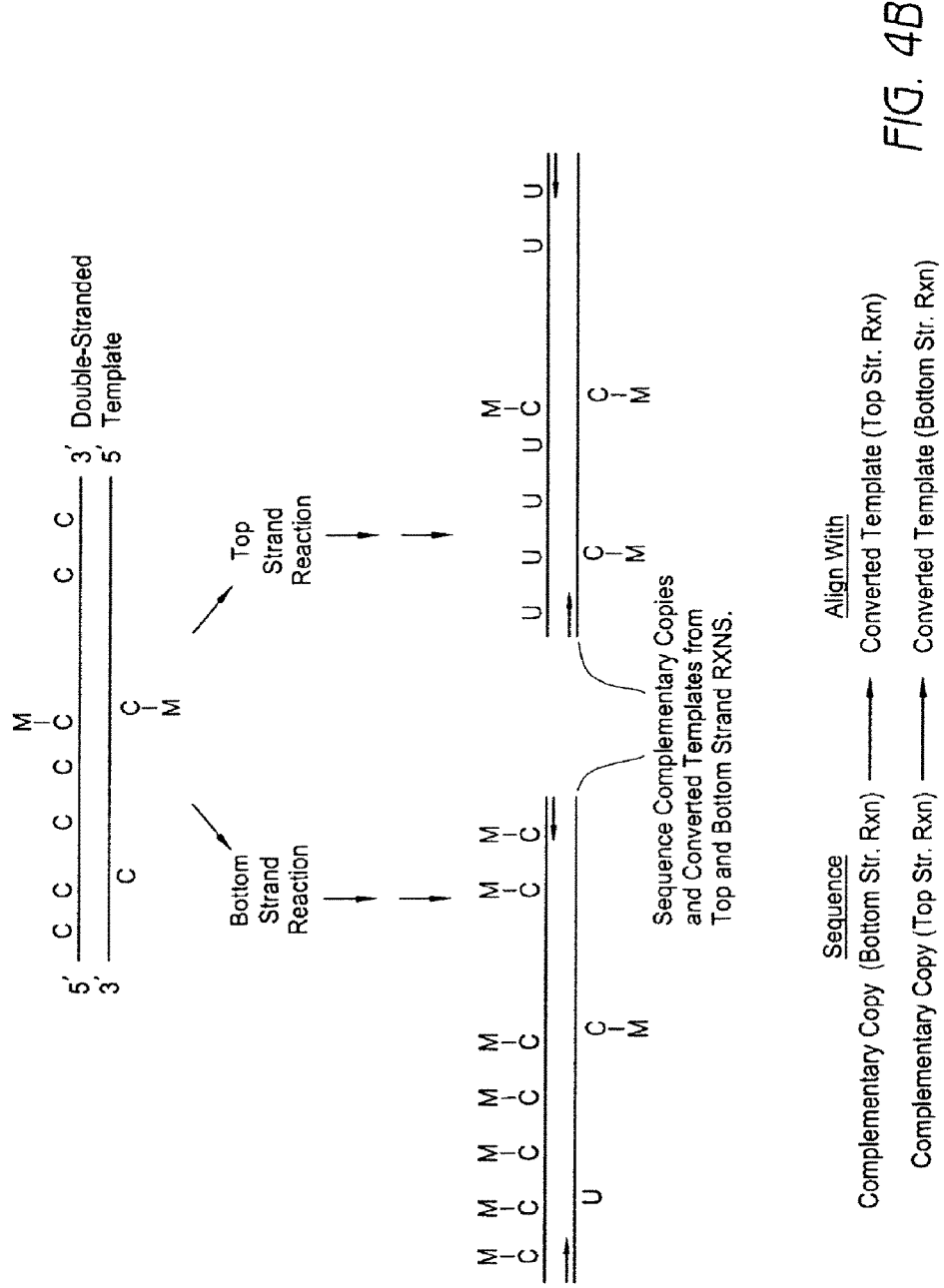

This extra manipulation step can be avoided where, for example, both strands of a double-stranded template are subjected to the methods described herein. An example is set forth in FIG. 2, where complementary copies of both the top and bottom template strands are obtained. The resulting products from this process can then be used to obtain and align sequence data from the top and bottom strands, as well as their complementary copies. An example is shown in FIG. 4B. As set forth in FIG. 4B, it will be recognized that sequence data obtained from the bottom strand complementary copy will be in the same orientation as the top strand converted template. Thus, sequence data from the bottom strand complementary copy can be directly aligned with the sequence data from the top strand converted template.

Oligonucleotide Primers

In embodiments presented herein, an oligonucleotide primer is used to direct the generation of a complementary copy of the template nucleic acid. In certain embodiments, the oligonucleotide primer is capable of forming a hairpin loop (a "looped oligonucleotide"). Typically, such a looped oligonucleotide does not necessarily have any substantial complementarity to the template strand. For example, in multiplex embodiments where methylation status is to be determined for a plurality of target sequences, the sequence of the oligonucleotide primer (whether capable of forming a loop structure or not) can be designed to be sufficiently different from any of the target sequences to inhibit cross hybridization of the primer sequence to any target sequences. In certain embodiments, the looped oligonucleotide primer is ligated to the template nucleic acid prior to the step of generating the complementary copy. Thus, in such embodiments the resulting complementary copy is covalently coupled to the template nucleic acid. In multiplex embodiments, each of the different target sequences can be ligated to a universal looped primer such that the same oligonucleotide primer sequence is ligated to a plurality of different target sequences.

An example is shown in FIG. 1. As set forth in FIG. 1, an oligonucleotide primer, shown here as a looped oligonucleotide, is ligated to the 3' end of the template strand. The looped oligonucleotide has a region of self-complementarity which forms a loop and a stem with a free 3' OH group. This region of complementarity, which forms the stem of the loop, need only be of sufficient length and complementarity to create a transient stem-loop structure which can maintain its duplexed form long enough to permit the initiation of strand synthesis by a polymerase. A nucleic acid polymerase is then used to extend the oligonucleotide primer in a 5'→3' direction in the presence of a bisulfate-resistant cytosine analog such as 5-methyl dCTP. The resulting product is a complementary strand that is covalently linked to the template strand via the looped oligonucleotide, forming an (imperfect) inverted repeat. One part of the inverted repeat represents the exact genomic sequence, where cytosines are methylated, while the other part is informative of the methylation status.

However, in certain embodiments, the oligonucleotide primer can be complementary to a portion of the template strand, regardless of whether the oligonucleotide primer is capable or not of forming a hairpin loop. Typically in such embodiments, the oligonucleotide primer is complementary to a region of the template which is located 3' of the region of interest. Complete complementarity is not required, but only a level of complementarity sufficient to allow the oligonucleotide primer to prime the formation of the complementary strand. Thus, in certain embodiments, an oligonucleotide can be used which is complementary to a 3' region of the template nucleic acid. In embodiments where the oligonucleotide primer is a looped oligonucleotide, the looped oligonucleotide is not necessarily ligated to the template nucleic acid prior to the step of generating a complementary copy.

In some embodiments, the oligonucleotide primer can comprise sequence complementary to a sequencing primer and/or to a capture probe. Sequencing primers can be used in later steps to facilitate sequencing of the template nucleic acid, the complementary copy, or both. The use of sequencing primers to determine the nucleotide sequence of the template nucleic acid or the complementary copy is described in further detail below.

In some embodiments, a second oligonucleotide primer can be ligated to the complementary copy. Typically, ligation of a second oligonucleotide primer is performed after the complementary copy is generated. Further, ligation of a second oligonucleotide primer often occurs prior to bisulfate treatment, however the order is not critical. The use of such a second oligonucleotide primer can facilitate other downstream manipulation of the complementary copy and/or the template nucleic acid. For example, such a second oligonucleotide primer can comprise sequence complementary to a sequencing primer. Sequencing primers can be used in later steps to facilitate sequencing of the template nucleic acid, the complementary copy, or both. As another example, such a second oligonucleotide primer can comprise sequence complementary to a capture probe. A second oligonucleotide primer that is ligated to a complementary copy or other nucleic acid target in a multiplex method can have a sequence that is non-complementary to target sequences presenting a multiplex mixture to be analyzed and can have universal sequence such that the same primer sequence is ligated to different target sequences in the multiplex mixture.

In general, capture probes are probes that are attached to a surface or another molecule. Capture probes can be specific for one or a limited number of complementary nucleic acid sequences. For example, capture probes can comprise one or more sequences complementary to unique, distinct, standardized, substantially similar, or identical tag sequences which are present in a set of nucleic acids of interest. Such capture probes will bind to nucleic acids which comprise the corresponding (complementary) tag sequence. For example, capture probes can be designed to specifically bind sequences in the oligonucleotide primers described above.

Nucleic Acid Pairs

Additional embodiments provided herein include tagged nucleic acid pairs. Preferred embodiments include a nucleic acid pair comprising a template nucleic acid comprising a cytosine residue; a complementary copy of the template nucleic acid having every cytosine methylated; and a tag capable of identifying the template nucleic acid and the complementary copy of the template nucleic acid as members of the nucleic acid pair, wherein the template nucleic acid and the complementary copy of the template nucleic acid are coupled to the tag. Other embodiments include vectors comprising such nucleic acid pairs.

In certain embodiments of the present invention, the tag is a molecule or nucleic acid sequence that is incorporated into an oligonucleotide primer used to generate the nucleic acid pair. In some embodiments, the tag is a molecule or nucleic acid sequence that is incorporated into a partner oligonucleotide. In some embodiments, the template nucleic acid can be covalently coupled to a partner oligonucleotide. Thus, in such embodiments, the oligonucleotide primer and the partner oligonucleotide each comprise a unique or distinct tag sufficient to identify the template nucleic acid and the complementary copy.

As used herein, the terms "partner oligonucleotide," "oligonucleotide tag" and like terms refer to an oligonucleotide which comprises a unique tag sufficient to identify the template nucleic acid and the complementary copy. Alternatively, the tag can be a tag that is distinct enough from other tags to distinguish it from the other tags. A set of oligonucleotide tags can be formed from a length of sequence that is sufficient to distinguish a collection of target nucleic acid fragments of a particular complexity. In general, longer tag sequences allow a larger number of individual target molecules to be distinguished. A set of tags can have, for example, 4, 5, 6, 8, 10, 15 or 20 nucleotides. In some embodiments, the tags may be longer than 20 nucleotides. The foregoing exemplary lengths can constitute an average, maximum or minimum length for the tags in a set.

Embodiments utilizing tags are especially useful in methods and compositions that include or comprise a plurality of the same, similar and/or different nucleic acids. Such embodiments are often referred to as multiplex embodiments. In these multiplex embodiments, the methods are performed using and the compositions comprise a population of nucleic acids. In some embodiments, the population of nucleic acids may be divided into one or more sub-populations.

For example, in multiplex embodiments, genomic DNA is often used as a source of template nucleic acid. In such embodiments, preferred methods utilize cutting or shearing techniques to cut the nucleic acid sample containing the target sequence into a size that will allow sufficient coverage of the target sequence in sequencing reactions. This may be accomplished by shearing the nucleic acid through mechanical forces (e.g. sonication) or by cleaving the nucleic acid using restriction endonucleases. Alternatively, a fragment containing the target may be generated using polymerase, primers and the sample as a template, as in polymerase chain reaction (PCR). In addition, amplification of the target using PCR or LCR or related methods may also be done; this may be particularly useful when the target sequence is present in the sample at extremely low copy numbers. Accordingly, because these fragmentation methods result a plurality of randomly-generated fragments, a diverse set of unique or distinct tags can be useful in order to identify large numbers of nucleic acid pairs.

Unique and/or different identifying tags are known in the art and can include, for example, fluorescent, radiolabel or nucleic acid tags. Fluorescent reporter dyes, are known in the art and can be used in the embodiments described herein. For example, by varying both the composition of the mixture (i.e. the ratio of one dye to another) and the concentration of the dye (leading to differences in signal intensity), matrices of unique optical signatures may be generated. The dyes may be chromophores or phosphors but are preferably fluorescent dyes, which due to their strong signals provide a good signal-to-noise ratio for identifying unique or distinct tags. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference.

Also particularly useful are nucleic acid tags. Where the unique or distinct tag is a nucleic acid sequence, the tag can be any nucleic acid sequence long enough to be unique or sufficiently distinct among other tag sequences used in the same assay. Thus, partner oligonucleotides which comprise a unique or distinct tag will specifically hybridize with a probe having a nucleotide sequence complementary to the unique or distinct tag. In certain embodiments, the template nucleic acid and the complementary copy each can comprise a tag that is unique or distinct when compared to tags present in other pairs but which is identical when compared to each other. In other embodiments, the unique or distinct tag in the template nucleic acid can be complementary to the unique or distinct tag in the complementary copy such that each tag is unique with regard to tags present in other pairs and with regard to tags within the same pair.

In certain aspects of the above embodiments, the template nucleic acid is double-stranded. In other aspects, the template nucleic acid is single-stranded. In certain other aspects, the template nucleic acid is single-stranded and the complementary copy is single-stranded. In certain aspects, the tag is, or is included in, a molecule disposed between the template nucleic acid and the complementary copy. Furthermore, in some embodiments, the molecule can comprise an oligonucleotide comprising a hairpin loop. In embodiments where the tag is a molecule that is disposed between the template nucleic acid and the complementary copy, neither unique nor distinct tag molecules need be used. In such embodiments, the nucleic acids are physically coupled via the molecule, thereby constituting an identifiable nucleic acid pair.

Figure 5A:
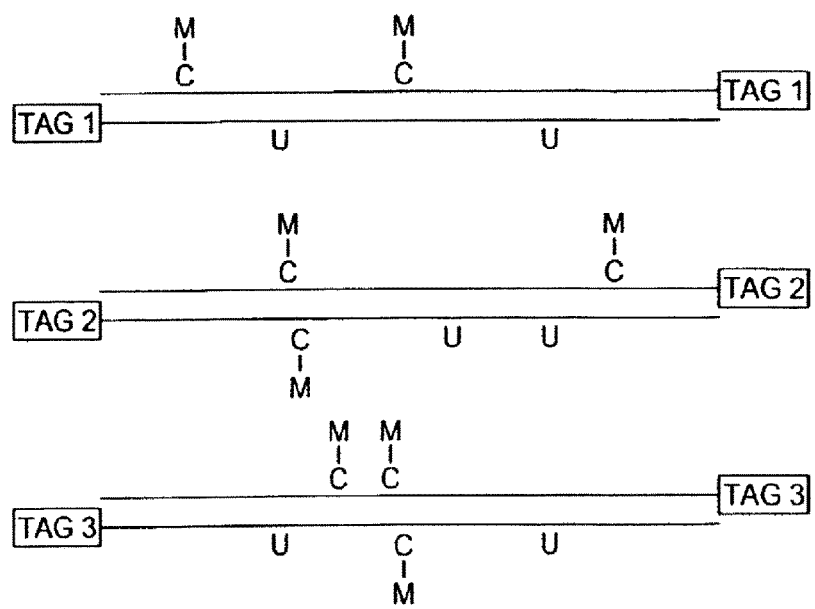
FIGS. 5A-B are schematic drawings showing nucleic acid pairs with tags.

In other aspects, the tag can comprise a first and second oligonucleotide comprising an identical nucleotide sequence, wherein the first oligonucleotide is coupled to the template nucleic acid and the second oligonucleotide is coupled to the complementary copy. One example is set forth in FIG. 5A, where each complementary copy and each corresponding template is coupled to a unique or distinct tag. The tag can comprise an oligonucleotide which comprises unique or distinct sequence. Thus, even where the two strands become separated in later reaction steps, the unique or distinct tag can be used to identify the template nucleic acid and the complementary copy as members of a nucleic acid pair. The entire sequence in the tag need not be unique or distinct. However, a portion of the tag can comprise sequence that identifies the template nucleic acid and the complementary copy as members of a nucleic acid pair.

Figure 5B:
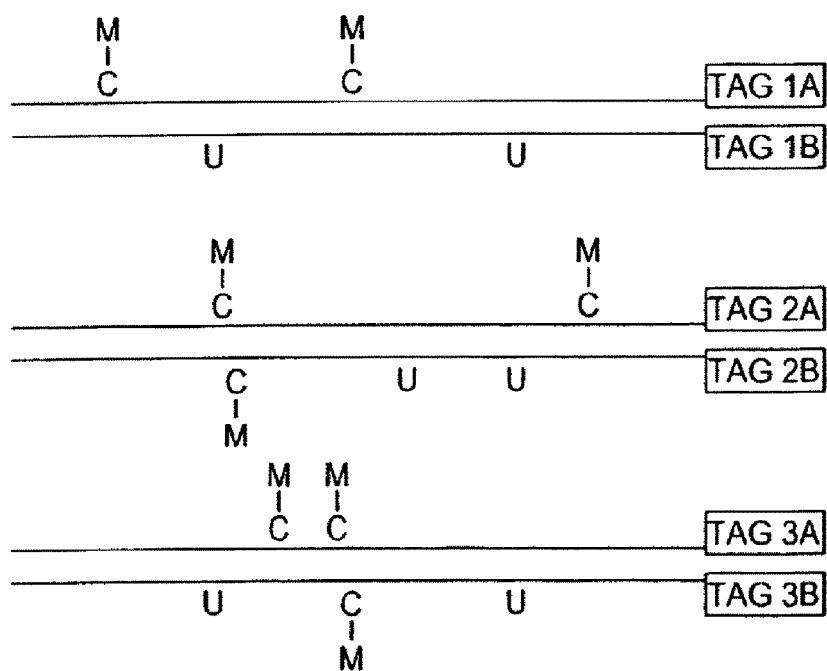

In other aspects, the tag comprises a first and second oligonucleotide comprising complementary nucleotide sequence, wherein the first oligonucleotide is coupled to the template nucleic acid and the second oligonucleotide is coupled to the complementary copy. One example is set forth in FIG. 5B, where each complementary copy and each corresponding template is coupled to an oligonucleotide, having at least some sequence within each oligonucleotide that is complementary to the other. The entire sequence in the tag need not be unique or distinct. However, at least a portion of the tag can comprise the complementary oligonucleotides which comprise a unique or distinct tag. A portion of the tag can comprise sequence that identifies the template nucleic acid and the complementary copy as members of a nucleic acid pair. Thus, even where the two strands become separated in later reaction steps, the unique or distinct tag can be used to identify the template nucleic acid and the complementary copy as members of a nucleic acid pair.

Removing and Trimming Repeats

Also presented herein are further methods of processing the template nucleic acid and complementary copy. Where a looped oligonucleotide is used to generate a complementary copy having bisulfite-resistant cytosine analogs and the resulting looped complement is converted by bisulfite treatment, the resulting product is typically an imperfect inverted repeat. When DNA is used, for example, the product is an imperfect inverted repeat because C:G base pairing is disrupted at sites where unmethylated cytosine is converted to uracil. However, in certain situations where inverted repeats present problems with later sequencing and/or alignment steps, the repeats may be manipulated so that the methylated complementary copy and the converted template sequences are present on the same strand in a parallel, rather than inverted, orientation.

Thus, also presented herein are methods of removing an inverted repeat. In one embodiment, a copy of the converted template is first generated after bisulfite conversion. Next, the 3' end of the complementary copy is ligated to the 5' end of the copy of the converted template. Finally, the strand is broken such that the complementary copy is no longer coupled to the converted template nucleic acid.

Figure 6A:
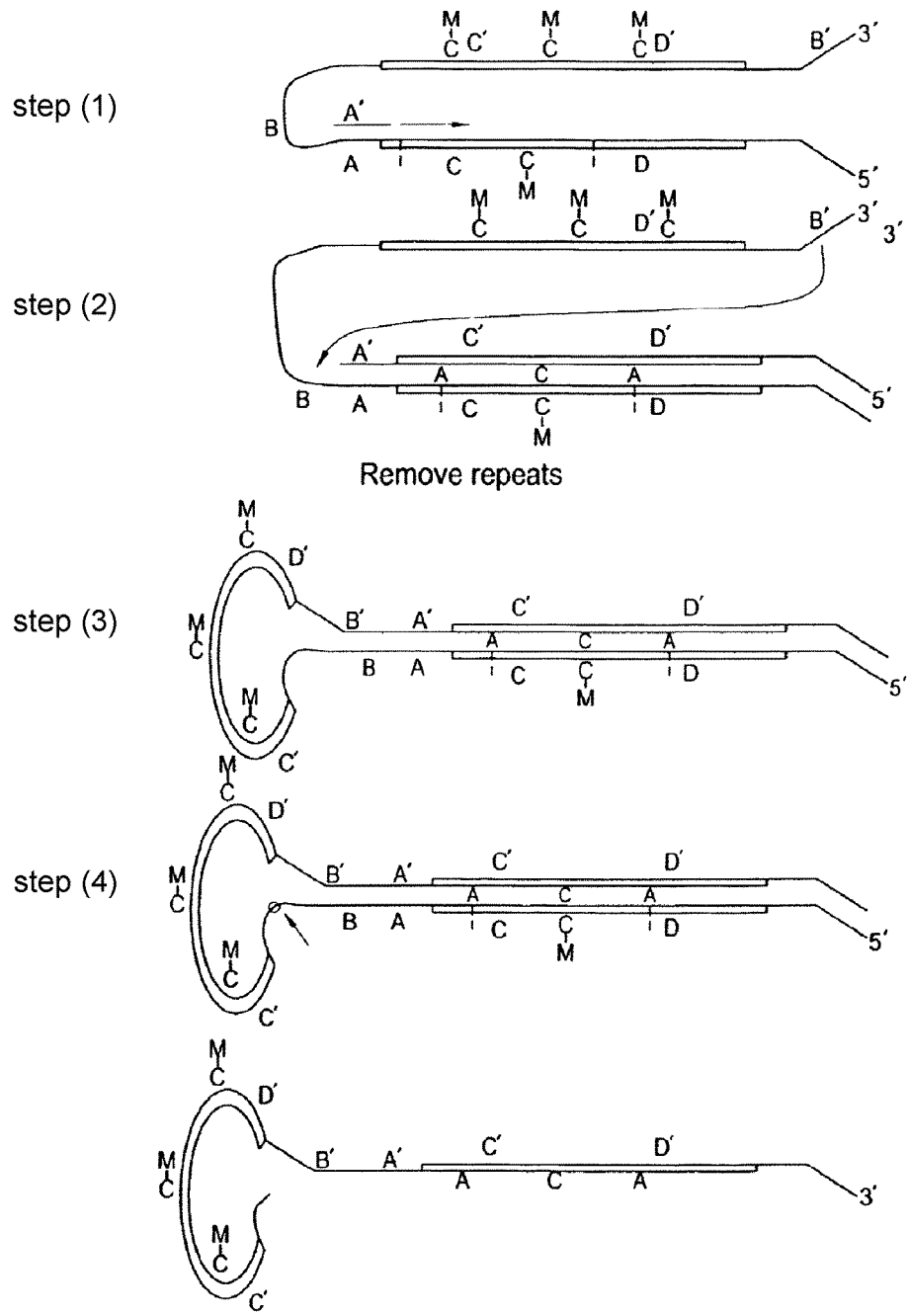
FIGS. 6A-B are schematic drawings showing removal and trimming of repeats.

FIG. 6A shows an example of this embodiment. A fragment comprising a looped, methylated copy of a template nucleic acid is provided. As described hereinabove, the fragment has been subjected to bisulfite conversion and bears an additional oligonucleotide coupled to the 3' end of the complementary copy. The orientation of the sequence is an imperfect inverted repeat (5' D-C . . . C'-D' 3'). As set forth in FIG. 6A, after bisulfite conversion, a copy of the converted template is generated using an oligonucleotide primer (A') with complementarity to a region (A) of the hairpin loop. Then, an intermolecular annealing is performed between the additional oligonucleotide (B') coupled to the 3' end of the complementary copy and a region (B) of the hairpin loop adjacent to the 5' end of the primer is used to make a copy of the converted template. The 3' end of the additional oligonucleotide (B') is ligated to the 5' end of the oligonucleotide primer (A'), and a strand break is induced in a region of the hairpin loop just 5' of region (B). In the embodiment shown in FIG. 6A, the break is a chemical break induced using a sensitive group incorporated in the hairpin loop. However, it will be appreciated that any other suitable method (e.g., restriction endonuclease) can be used to induce a single-strand break. The resulting product is shown at the bottom of FIG. 6A, and comprises the methylated complementary copy coupled to the 5' end of the copy of the converted template. The complementary copy and the copy of the converted template are separated by a region comprising the two primers (B' and A') used in this method. After this manipulation, the orientation of the repeat sequence is now direct (5' C'-D' C'-D' 3'), rather than inverted.

In certain sequencing settings, it is desirable to shorten the length of a sequence to remove repeat regions in the sequence. Thus, presented herein are additional methods that can be used to trim the fragment generated in the above-described method in order to remove repeat regions. If the fragment is single stranded, a copy of the fragment is made using a primer that is complementary to the 3' end of the fragment, creating a double-stranded molecule. Next, a double-stranded adapter molecule is ligated to one end of the molecule. The adapter can comprise, for example, a recognition site for a restriction endonuclease. In some embodiments, the restriction endonuclease will be a type III restriction endonuclease, which typically cuts about 20-30 bp away from the recognition site. For example, the type III endonuclease EcoP15I has a cleavage site 27 bp away from the enzyme recognition site. Additionally, the fragment can bear an additional oligonucleotide coupled to the 5' end of the converted template. This additional oligonucleotide can also comprise a recognition site for a restriction endonuclease such as EcoP15I. The process of ligating adapter molecules with subsequent endonuclease trimming can be repeated until the fragment has been trimmed to the desired length. Thus, for example, after two rounds of trimming with an endonuclease, a 100 nucleotide fragment can be converted to a 46 nucleotide fragment.

Figure 6B:
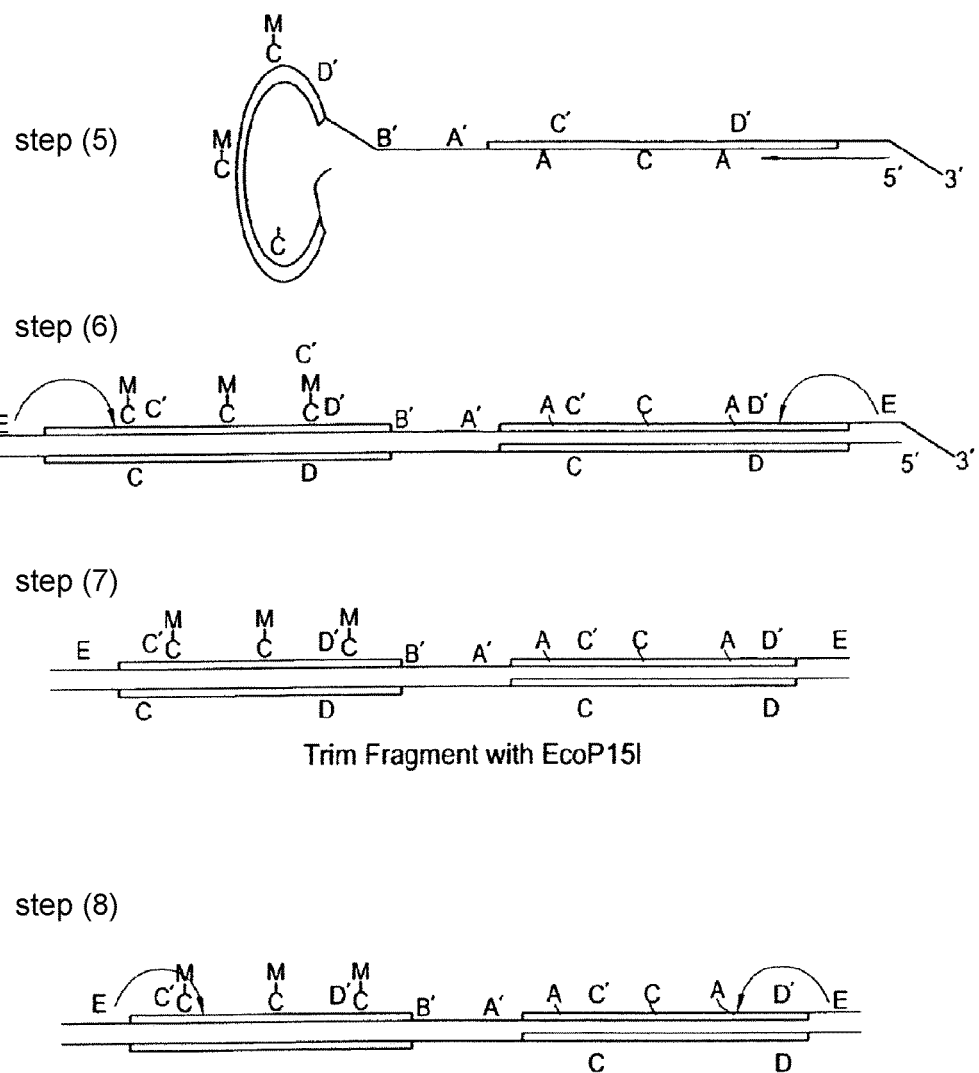

FIG. 6B shows the additional trimming reaction that can be performed to remove additional repeats. A fragment is provided and a copy is made by extending an oligonucleotide primer using a nucleic acid polymerase. As shown in FIG. 6B, a double-stranded adapter molecule is blunt-end ligated to the double-stranded fragment. The adapter molecule comprises an EcoP15I recognition site. Additionally, the fragment bears an additional oligonucleotide coupled to the 5' end of the converted template. This additional oligonucleotide comprises an EcoP15I recognition site. Thus, the double-stranded fragment is trimmed in both directions. The process of annealing and ligating EcoP15I site adapters is repeated using a pool of adapters with a degenerate 2-base overhang. After ligation of the adapters, the endonuclease reaction is repeated. The resulting product is a fragment where 54 nucleotides have been removed from each end.

Other Methods of Tracking Complementary Strands

Also provided herein are additional methods of keeping track of sequence and methylation information in complementary strands after the strands have been subjected to bisulfite conversion of nucleic acids. These additional embodiments relate to pairing the bisulfite-converted sequence of both strands of a double-stranded nucleic acid and using the sequence information from both strands to determine the sequence and/or methylation status of one or both strands prior to bisulfite conversion. The pairing can be achieved, for example, by a physical tether between strands or by the presence of tag sequences on each strand that identify the strands as being paired. Thus, these embodiments preserve sequence and methylation information of a template strand and can be performed, for example, without the step of generating a complementary strand comprising bisulfite-resistant cytosine analogs.

In some such embodiments, a method of identifying methylated cytosines in a nucleic acid comprises the steps of obtaining a template nucleic acid comprising at least a first methyl CpG dinucleotide, obtaining a complementary copy of the template nucleic acid, wherein the complementary copy comprises a complementary methyl CpG dinucleotide in a position opposite the first methyl CpG dinucleotide and subjecting the template nucleic acid and the complementary copy to bisulfite treatment to convert unmethylated cytosine residues in the template nucleic acid into uracil residues, thereby resulting in a bisulfite-converted template nucleic acid and a bisulfite-converted converted complementary copy. Using the bisulfite-converted nucleic acids, the nucleotide sequence of the template nucleic acid and the nucleotide sequence of the bisulfite-converted complementary copy can be determined. The nucleotide sequence of the bisulfite-converted complementary copy can then be compared to the nucleotide sequence of the bisulfite-converted template nucleic acid, so as to determine the nucleotide sequence of the template nucleic acid prior to bisulfite conversion and the methylation status of the template nucleic acid prior to bisulfite conversion.

Figure 7:
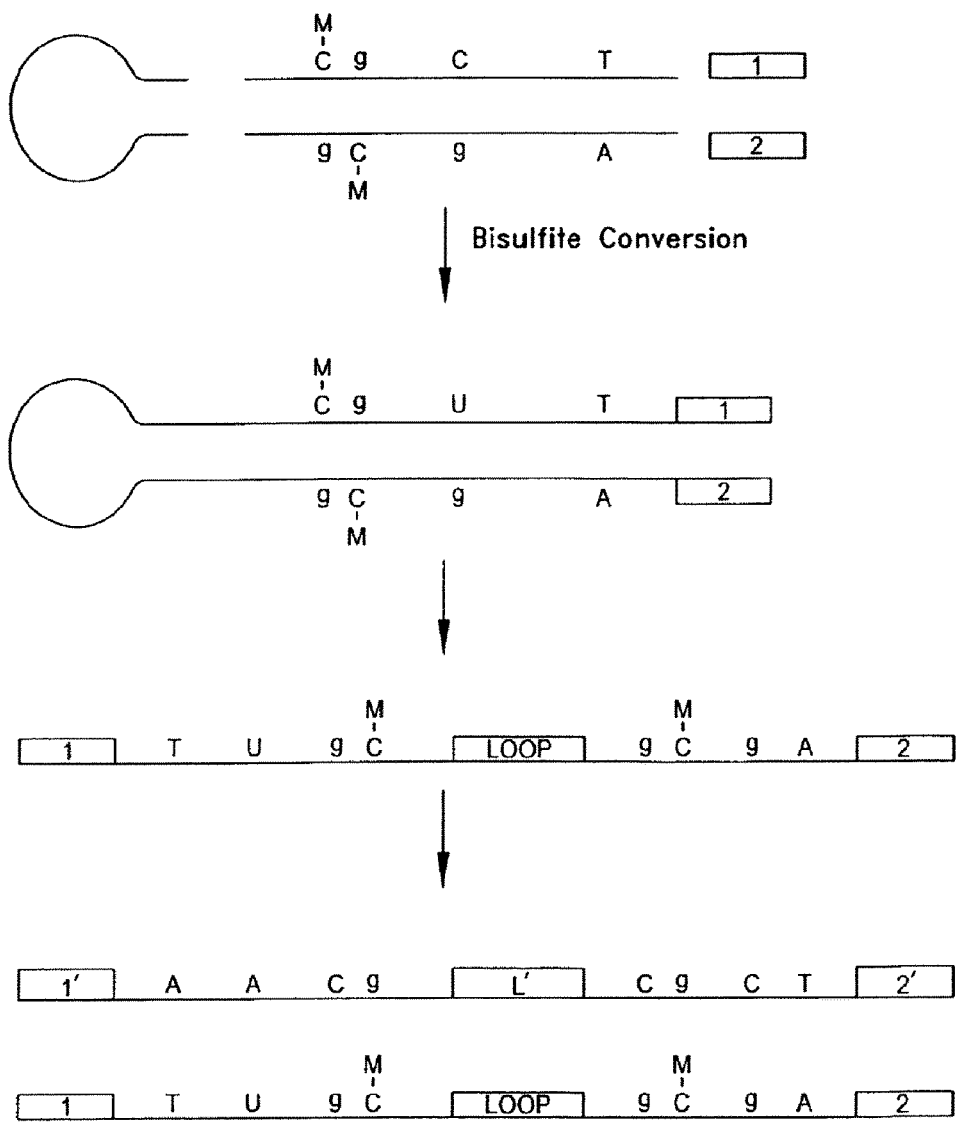
FIG. 7 is a schematic drawing showing bisulfite conversion and sequencing of both top and bottom strands of a template nucleic acid. Top and bottom strands are linked together using a looped oligonucleotide. After bisulfite conversion, the hairpin loop is unfolded and a complementary copy is generated. Adapter oligonucleotides on the 5' and 3' ends are used for priming sequencing reactions and for capture using capture probes.

An exemplary embodiment is set forth in FIG. 7, in which a double-stranded template nucleic acid is provided. The template nucleic acid comprises a template strand and a complementary copy strand. As set forth in FIG. 7, where a methylated cytosine appears in the context of a CpG dinucleotide in the template strand, the complementary strand comprises a methyl CpG dinucleotide in a position opposite and complementary to the CpG dinucleotide in the template strand. The template and complementary strands are linked together using a looped oligonucleotide, forming a hairpin loop. As set forth in FIG. 7, after bisulfite conversion, the hairpin loop is unfolded, forming a single-stranded molecule which comprises the template sequence at one end and the complementary copy at the other end. A complementary copy of the single-stranded molecule can then be generated, so as to form a duplex nucleic acid which can then be used for sequencing purposes. Adapter oligonucleotides on the 5' and 3' ends can be used for priming sequencing reactions and, for example, for capture using capture probes.

With reference to FIG. 7, both the template strand and the complementary strand can be sequenced. In particular, the nucleotide sequence of the bisulfite-converted template nucleic acid (i.e., the region between adapter sequence (2) and the loop sequence) can be determined. Additionally, the nucleotide sequence of the bisulfite-converted complementary copy (i.e., the region between adapter sequence (1) and the loop sequence) can be determined. By comparing the nucleotide sequences of the two bisulfite-converted regions, the methylation status of the template nucleic acid prior to bisulfite conversion can be determined. Similarly, by comparing the nucleotide sequences of the two bisulfite-converted regions, the nucleotide sequence of the template nucleic acid prior to bisulfite conversion can be determined. One example of making such a comparison is set forth in the table below.

TABLE 1

Comparison of Bisulfite-Converted Sequences to Determine Methylation Status and Sequence Prior to Bisulfite Conversion.

| First fragment read | Second fragment read, equivalent position | Sequence and Methylation Status Prior to Bisulfite Conversion (first/second) |
|---|---|---|
| T | G | unmeth C/G |
| T | A | T/A |
| G | T | G/unmeth C |
| A | T | A/T |
| C | G | methC/G |
| G | C | G/methC |

The method described above and depicted in FIG. 7 is just one aspect of the embodiment. It will be appreciated that other variations of such methods can be employed in the embodiment described herein. For example, where a looped oligonucleotide is used to create a physical tether between the two strands of double-stranded nucleic acid, the hairpin can be unfolded either prior to or after bisulfite-conversion.

It will also be appreciated that the bisulfite-converted complementary copy and the bisulfite-converted template nucleic acid can be paired without using a physical tether. For example, the template nucleic acid and complementary copy can be paired via tag molecules which identify the bisulfite-converted complementary copy and the bisulfite-converted template nucleic acid as members of a nucleic acid pair. The use of tag molecules is described elsewhere herein and can be applied to the present embodiments. Thus, for example, adapter oligonucleotides may be ligated to the template and complementary nucleic acid molecules. The adapter oligonucleotides, can then be used to identify the bisulfite-converted template and the bisulfite-converted complementary copy as members of a nucleic acid pair. It will be appreciated that other tag molecules can include dyes and/or any other molecules that can be grouped or paired.

Bisulfite Conversion and Detection of Methylation Status

Methylation of CpG dinucleotide sequences can be measured by employing cytosine conversion based technologies. The term "conversion" as used herein means the conversion of an unmethylated cytosine to another nucleotide which will distinguish the unmethylated from the methylated cytosine. Typically, the agent modifies unmethylated cytosine to uracil. A commonly-used agent for modifying unmethylated cytosine preferentially to methylated cytosine is sodium bisulfite. However, other agents that similarly modify unmethylated cytosine, but not methylated cytosine, can also be used in the method of the invention. Sodium bisulfite ($NaHSO_3$) reacts readily with the 5,6-double bond of cytosine, but poorly with methylated cytosine, as described by Olek A., Nucleic Acids Res. 24:5064-6, 1996 or Frommer et al., Proc. Natl. Acad. Sci. USA 89:1827-1831 (1992), each of which is incorporated herein by reference. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and other polymerases and therefore upon PCR or during a sequencing reaction, the resultant product contains cytosine only at the position where 5-methylcytosine occurs in the starting template nucleic acid.

Bisulfite-treated nucleic acids, such as DNA, can subsequently be analyzed by conventional molecular techniques, such as PCR amplification, sequencing, and detection comprising oligonucleotide hybridization. As described below, a variety of techniques are available for sequence-specific analysis (e.g., MSP) of the methylation status of one or more CpG dinucleotides in a particular region of interest. The methods provided herein are particularly useful for creating an archived complementary copy of the pre-conversion sequence for each of a multitude of genomic fragments. The archived copy may be covalently linked to the bisulfite-converted template. Alternatively, the archived copy may not be covalently linked to the bisulfite-converted template, but rather the archived copy and the bisulfite-converted template may be informationally linked via the unique or distinct tag sequences described above, which are either substantially identical to each other or substantially complementary to each other.

Thus, although many of the embodiments set forth herein are specifically described in the context of determining the nucleotide sequence of the bisulfite-converted template nucleic acid and a non-converted complementary copy, the bisulfite-converted template nucleic acid may be used as a template for other methylation detection techniques, such as MSP, Ms-SNuPE, MethylLight™, and others known in the art. In such uses, the complementary copy is useful for example, to confirm the genomic context of the template nucleic acid or as a means for designing site-specific primers for such techniques.

Techniques for the analysis of bisulfite treated DNA can employ methylation-sensitive primers for the analysis of CpG methylation status with isolated genomic DNA as described by Herman et al., *Proc. Natl. Acad. Sci. USA* 93:9821-9826, 1996, and in U.S. Pat. Nos. 5,786,146 and 6,265,171, each of which is incorporated herein by reference. Methylation sensitive PCR (MSP) allows for the detection of a specific methylated CpG position within, for example, the regulatory region of a gene. The DNA of interest is treated such that methylated and non-methylated cytosines are differentially modified, for example, by bisulfite treatment, in a manner discernable by their hybridization behavior. PCR primers specific to each of the methylated and non-methylated states of the DNA are used in a PCR amplification. Products of the amplification reaction are then detected, allowing for the elucidation of the methylation status of the target locus, such as a target CpG site, within the genomic DNA. Other methods for the analysis of bisulfite treated DNA include methylation-sensitive single nucleotide primer extension (Ms-SNuPE) (Gonzalgo & Jones, *Nucleic Acids Res.* 25:2529-2531, 1997; and see U.S. Pat. No. 6,251,594, each of which is incorporated herein by reference), and the use of real time PCR based methods, such as the art-recognized fluorescence-based real-time PCR technique MethyLight™. (Eads et al., *Cancer Res.* 59:2302-2306, 1999; U.S. Pat. No. 6,331,393; and Heid et al., *Genome Res.* 6:986-994, 1996, each of which is incorporated herein by reference).

Methods such as those set forth above can be used to determine the methylation level and/or pattern of at least one locus in a sample DNA of interest. In some embodiments, one locus on the sample DNA is measured. In other embodiments the methylation level for a plurality of loci is determined. In some embodiments, methylation levels and/or patterns for large pluralities of loci can be determined using a nucleic acid array. A nucleic acid array provides a convenient platform for simultaneous analysis of large numbers of loci including, for example, at least 2, 3, 4, 5, 6, 7, 8, 9, 10, 50, 100, 500, 1000, 5000, 10,000, 100,000, $10^6$, $10^7$ or more loci. Methods set forth herein can be used to analyze or evaluate such pluralities of loci simultaneously or sequentially as desired. In particular embodiments, a plurality of different probe molecules can be attached to a substrate or otherwise spatially distinguished in an array. Each probe is typically specific for a particular locus and can be used to distinguish methylation status of the locus. Exemplary arrays that can be used in the invention include, without limitation, slide arrays, silicon wafer arrays, liquid arrays, bead-based arrays and others known in the art or set forth in further detail below.

Determination of Nucleotide Sequence

The methods provided herein include the steps of determining the nucleotide sequence of bisulfite-converted template nucleic acid and a non-converted complementary copy of the template nucleic acid. In a preferred embodiment, the nucleic acid is DNA. Methods of determining a nucleotide sequence of interest are known in the art, and any such method can suitably be used to determine the nucleotide sequence of the bisulfite-converted template nucleic acid and/or the complementary copy of the template. The methods and nucleic acid compositions provided herein are particularly useful in array-based sequencing methodologies, where large numbers of molecules may be sequenced in parallel. Array-based sequencing methodologies are known in the art. Accordingly, it will be apparent to one of skill in the art that any of a variety of arrays may be used to determine the nucleic acid sequences of interest. Particularly useful are arrays that utilize clonal amplification of single molecules or, alternatively, arrays wherein single molecules are detected individually.

For embodiments that include clonal amplification any of a variety of methods can be used. Several amplification methods will be exemplified below in the context of commercial sequencing products or other sequencing systems. It will be understood that amplification methods and sequencing methods can by used in various combinations and the examples below are provided for purposes of explanation and are not intended to wed any particular amplification method to any particular sequencing method.

Useful methods for clonal amplification from single molecules include rolling circle amplification (RCA) (Lizardi et al., *Nat. Genet.* 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., *Nucl. Acids Res.* 28:E87 (2000); Pemov et al., *Nucl. Acids Res.* 33:e11 (2005); or U.S. Pat. No. 5,641,658, each of which is incorporated herein by reference), polony generation (Mitra et al., *Proc. Natl. Acad. Sci. USA* 100:5926-5931 (2003); Mitra et al., *Anal. Biochem.* 320:55-65 (2003), each of which is incorporated herein by reference), and clonal amplification on beads using emulsions (Dressman et al., *Proc. Natl. Acad. Sci. USA* 100:8817-8822 (2003), which is incorporated herein by reference) or ligation to bead based adapter libraries (Brenner et al., *Nat. Biotechnol.* 18:630-634 (2000); Brenner et al., *Proc. Natl. Acad. Sci. USA* 97:1665-1670 (2000)); Reinartz, et al., *Brief Funct. Genomic Proteomic* 1:95-104 (2002), each of which is incorporated herein by reference).

A successful approach to generation of clonal arrays is the use of polonies originally described by Mitra et al. (*Nucleic Acids Res.* 27:e34 (1999)). Polonies are generated by some form of solid-phase amplification by primers attached to a surface (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., *Nucl. Acids Res.* 28:E87 2000); Mitra and Church, *Nucleic Acids Res.* 27:e34 (1999)).

Bridge amplification is also useful, for example, as carried out in a commercial sequencing platform from Solexa (Hayward Calif., subsequently acquired by Illumina Inc) (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Dressman et al., *Proc. Natl. Acad. Sci. USA* 100:8817-8822 (2003); Mitra and Church, *Nucleic Acids Res.* 27:e34 (1999)). The Solexa sequencing platform employs solid-phase bridge PCR using a pair of PCR primers immobilized to a slide surface. Repeated cycles of denaturation and polymerase extension lead to amplification of the target molecule on the solid phase surface. Bridge amplification, with its immobilized primers, can be performed with thermocycling or isothermally by physically exposing the surface to alternating cycles of denaturation and extension.

Templates may be amplified on beads, for example using emulsion PCR techniques. In emulsion PCR techniques a population of beads is provided having a first primer attached to each bead. The beads and template DNA are mixed in an emulsion at a concentration where, on average, no bead-containing oil droplet will contain more than one template. A template can hybridize to a bead via hybridization of the primer on the bead to a primer that was previously ligated to the template. Following PCR amplification the beads will contain multiple copies of a single template Sequence. Exemplary emulsion-based amplification techniques that can be used in a method of the invention are described in US 2005/0042648; US 2005/0079510; US 2005/0130173 and WO 05/010145, each of which is incorporated herein by reference.

After an array of clonal features is created, the array can be subjected to cycle sequencing consisting of repeated rounds of sequencing biochemistry interspersed by imaging. Several formats of cycle sequencing have been described in the literature, and include sequencing-by-synthesis (SBS), sequencing-by-ligation (SBL), and sequencing-by-hybridization (SBH). One of the most useful forms of cycle sequencing is SBS, in which the sequence of a template, for example, in a polony or amplicon, is read by repeated rounds of polymerase-based nucleotide insertion and fluorescent/chemiluminescent readout. Tow exemplary formats of SBS are: (1) stepwise nucleotide addition (SNA) employing cycles of dNTP incorporation and imaging, and (2) cyclic reversible termination (CRT) employing cycles of incorporation of reversible terminators, imaging, and deprotection.

Sequencing can be carried out using any suitable sequencing technique, wherein nucleotides are added successively to a free 3' hydroxyl group, resulting in synthesis of a nucleic acid chain in the 5' to 3' direction. The nature of the nucleotide added is preferably determined after each nucleotide addition. Sequencing techniques using sequencing by ligation and techniques such as massively parallel signature sequencing (MPSS) where bases are removed from, rather than added to the strands on the surface are also useful, as are techniques using detection of pyrophosphate release (pyrosequencing).

The initiation point for a sequencing reaction may be provided by annealing of a sequencing primer to a target nucleic acid present at a feature of an array. In this connection, a known adapter region that is present on a target nucleic acid, for example, as a result of a reaction described previously herein, can be used as a priming site for annealing of a sequencing primer. For example, a sequencing primer can be annealed to a priming site that was ligated to a target sequence prior to bisulfite treatment.

In a particular embodiment, a nucleic acid sequencing reaction can include steps of hybridising a sequencing primer to a single-stranded region of a linearized amplification product, sequentially incorporating one or more nucleotides into a nucleic acid strand complementary to the region of amplified template strand to be sequenced, identifying the base present in one or more of the incorporated nucleotide(s) and thereby determining the sequence of a region of the template strand.

One preferred sequencing method utilizes modified nucleotides having removable 3' blocks, for example, as described in WO 04/018497 and U.S. Pat. No. 7,057,026, the contents of which are incorporated herein by reference. Once the modified nucleotide has been incorporated into the growing nucleic acid chain complementary to the region of the template being sequenced there is no free 3'-OH group available to direct further sequence extension and therefore the polymerase can not add further nucleotides. This allows convenient detection of single nucleotide incorporation events. Once the identity of the base incorporated into the growing chain has been determined, the 3' block may be removed to allow addition of the next successive nucleotide. By ordering the products derived using these modified nucleotides, it is possible to deduce the DNA sequence of the DNA template. Multiple reactions can be carried out in parallel on a single array, for example, if each of the modified nucleotides has a different label attached thereto, known to correspond to the particular base, thereby facilitating discrimination between the bases added during each incorporation step. If desired, a separate reaction may be carried out for each of the modified nucleotides.

Modified nucleotides used in an amplification or sequencing reaction may carry a label to facilitate their detection. A fluorescent label, for example, may be used for detection of modified nucleotides. Each nucleotide type may thus carry a different fluorescent label, for example, as described in WO 07/135368, the contents of which are incorporated herein by reference in their entirety. The detectable label need not, however, be a fluorescent label. Any label can be used which allows the detection of an incorporated nucleotide. Similarly, fluorescent labels or other labels can be used to detect any of a variety of analytes on an array.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in WO 07/123744, the contents of which are incorporated herein by reference in their entirety. Detectors that are capable of obtaining an image of an array surface such as those configured to scan an array surface. Such detectors can be configured to take a static image of an array surface, scan a point across an array surface or scan a line across an array surface. Exemplary scanning devices that can be used are described, for example, in U.S. Pat. No. 7,329,860, which is incorporated herein by reference. A detector can be configured to obtain an image of an array at high resolution, for example, in the low micron to submicron range. In particular embodiments, an image can be obtained at a Rayleigh resolution between 0.2 and 10 micrometers.

The invention is not intended to be limited to use of the sequencing method outlined above, as a variety of sequencing methodologies which utilize successive incorporation of nucleotides into a nucleic acid chain or removal of nucleotides from a nucleic acid chain can be used. Suitable alternative techniques include, for example, Pyrosequencing, FISSEQ (fluorescent in situ sequencing), MPSS and sequencing by ligation-based methods, for example as described is U.S. Pat. No. 6,306,597. Sequencing by hybridization methods can also be used. Further sequencing techniques, some of which relate to the above described methods are set forth in further detail below.

In one commercial implementation from 454 Lifesciences, (Branford, Conn.) and Roche Diagnostics (Basel, Switzerland), cyclic pyrosequencing from assembled clonal beads has been used to sequence entire genomes (Margulies et al., Nature 437:376-380 (2005), which is incorporated herein by reference). This approach provides high accuracy and throughput. Other examples of SNA in the literature include the methods described in combination with polony amplification by Mitra et al., supra, 2003. Cyclic addition of cleavable fluorescently-labeled dNTPs was used to sequence the polony clones. After each base addition and imaging step, fluorescent labels were cleaved by disulfide reduction. In a third approach described by Braslaysky et al., single target molecules were immobilized onto a glass microscope slide at a sparse density and performed cycle sequencing by basewise addition of Bodipy-labeled dNTPs (Braslaysky et al., Proc. Natl. Acad. Sci. USA 100:3960-3964 (2003), which is incorporated herein by reference). After imaging, the fluorescence was destroyed by photobleaching. Similar manipulations can be used to determine the sequence of a sample nucleic acid in accordance with the methods set forth herein.

In CRT, cycle sequencing is accomplished by stepwise addition of reversible terminator nucleotides containing a cleavable or photobleachable dye label. This approach is being commercialized by Solexa (now Illumina), and is also described in WO 91/06678, which is incorporated herein by reference. The availability of fluorescently-labeled terminators in which both the termination can be reversed and the fluorescent label cleaved is important to facilitating efficient CRT. Polymerases can also be co-engineered to efficiently incorporate and extend from these modified nucleotides. In particular embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, both disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination.

Paired-End Sequencing

A further sequencing methodology useful in the methods and arrays provided herein is paired-end sequencing. This methodology is described in greater detail in WO 2007/010252, WO 2007/091077 and WO 03/74734, each of which is incorporated by reference herein in its entirety. This approach utilizes pairwise sequencing of a double-stranded polynucleotide template, which results in the sequential determination of nucleotide sequences in two distinct and separate regions of the polynucleotide template. The paired-end methodology makes it possible to obtain two linked or paired reads of sequence information from each double-stranded template on a clustered array, rather than just a single sequencing read as can be obtained with other methods.

Paired end sequencing technology can make special use of clustered arrays, generally formed by solid-phase amplification, for example as set forth in the incorporated materials in WO 03/74734. Target polynucleotide duplexes, fitted with adapters, are immobilized to a solid support at the 5' ends of each strand of each duplex, for example, via bridge amplification as described above, forming dense clusters of double stranded DNA. Because both strands are immobilized at their 5' ends, sequencing primers are then hybridized to the free 3' end and sequencing by synthesis is performed. Adapter sequences can be inserted in between target sequences to allow for up to four reads from each duplex, as described in the incorporated materials in WO 2007/091077.

This pairwise approach is particularly useful for clustered arrays, and allows for rapid throughput because two linked or paired reads are provided from each double-stranded template, rather than a single sequencing read. Furthermore, this approach offers straightforward sample preparation, using different adapters to introduce two unique priming sites on opposite strands. In one application of this methodology, both primers can start sequencing with a T nucleotide to aid colocalization between the two reads.

In a further adaptation of this methodology, specific strands can be cleaved in a controlled fashion as set forth in the incorporated materials in WO 2007/010252. As a result, the timing of the sequencing read for each strand can be controlled, permitting sequential determination of the nucleotide sequences in two distinct and separate regions on complementary strands of the double-stranded template.

Arrays

Some of the embodiments provided herein relate to arrays and methods of making arrays, useful for determining the methylation status of one or more nucleic acid sequences. With respect to making such arrays, in a preferred embodiment, the method can include the steps of: providing a solid support with a plurality of sites; providing a sample comprising a template nucleic acid; generating a complementary copy of the template nucleic acid, the generating being directed by an oligonucleotide primer using a nucleic acid polymerase in the presence of a bisulfite-resistant cytosine analog such as 5-methyl dCTP, wherein the generating produces a complementary copy of the template nucleic acid such that each cytosine residue in the complementary copy is methylated; subjecting the template nucleic acid and the complementary copy to bisulfite treatment to convert unmethylated cytosine residues in the template nucleic acid into uracil residues, resulting in a bisulfite-converted template nucleic acid and a non-converted complementary copy; and coupling the template and the complementary copy of the template to the solid support. In certain aspects of the method, at least one of the sites comprises a capture probe. In such aspects, the capture probe can comprise a nucleotide sequence complementary to the template or the complementary copy of the template. In certain aspects, an oligonucleotide complementary to the capture probe is attached to the template or complementary copy of the template.

The template nucleic acids described above can be double-stranded or single-stranded. In certain embodiments, the oligonucleotide primer is capable of forming a hairpin loop. In such embodiments, the complementary copy can be covalently coupled to the template nucleic acid. Typically in such embodiments, the oligonucleotide primer is ligated to the template nucleic acid prior to the generating step. Also, in certain aspects the oligonucleotide primer can comprise sequence complementary to a sequencing primer and/or to a capture probe.

In some of the embodiments described above, the method can further comprise the step of ligating a second oligonucleotide primer to the complementary copy prior to bisulfite treatment. In such methods, the second oligonucleotide primer can comprise sequence complementary to a sequencing primer. Further, the second oligonucleotide primer can comprise sequence complementary to a capture probe. In some embodiments, both capture probe-complementary and sequencing primer-complementary sequences are included in the second oligonucleotide primer.

In certain embodiments, the oligonucleotide primer is covalently coupled to the complementary copy prior to bisulfate treatment, but not to the template nucleic acid. In such methods, the template nucleic acid is covalently coupled to a partner oligonucleotide, the oligonucleotide primer and the partner oligonucleotide comprising a unique tag sufficient to identify the template nucleic acid and the complementary copy.

Also provided herein are arrays useful for determining the methylation status of one or more nucleic acid sequences. In a preferred embodiment, the array comprises: a solid support with a plurality of sites, a bisulfate-converted template nucleic acid; and a non-converted complementary copy of the template nucleic acid; wherein the template nucleic acid is coupled to at least one of the plurality of sites and the non-converted complementary copy is coupled to at least one of the plurality of sites. In certain aspects the template nucleic acid is annealed to at least one of the plurality of sites and the non-converted complementary copy is annealed to at least one of the plurality of sites. It will be understood that more than one feature may be present at any one site. Thus, for example, in some aspects, the bisulfate-converted template nucleic acid and the non-converted complementary copy can be annealed to the same site. Also, multiple copies of the bisulfate-converted template nucleic acid, and/or multiple copies of the non-converted complementary copy, may all be present at the same site. In certain aspects, each cytosine residue is methylated in the non-converted complementary copy of the template nucleic acid. In certain aspects, each unmethylated cytosine residue in the bisulfate-converted template nucleic acid has been converted into a uracil residue.

In certain aspects, at least one of the sites comprises a capture probe. In certain aspects, the capture probe comprises a nucleotide sequence complementary to the template nucleic acid or the complementary copy of the template nucleic acid. In certain aspects, an oligonucleotide complementary to the capture probe is attached to the template or complementary copy of the template.

In particular embodiments the array comprises a plurality of different target nucleic acids and the target nucleic acids have target sequences that are different from each other but a universal priming sequence that is the same for all or at least a plurality of the target nucleic acids. The universal priming sequence can be used to sequence the different target sequences using universal primers that have a sequence, in common between them, that is complementary to the universal priming sequence.

In certain aspects of the above embodiments, the complementary copy is covalently coupled to the template nucleic acid. In certain aspects, a molecule is disposed between the template nucleic acid and the complementary copy of the template nucleic acid. In certain aspects, the molecule is an intervening oligonucleotide. In certain aspects, the intervening oligonucleotide is capable of forming a hairpin loop. In certain aspects, the intervening oligonucleotide comprises sequence complementary to a sequencing primer and/or to a capture probe. In certain aspects, an additional oligonucleotide is covalently coupled to the complementary copy. The additional oligonucleotide can comprise sequence complementary to a sequencing primer, or to a capture probe, for example.

In particular embodiments, the complementary copy is not covalently coupled to the template nucleic acid. In such embodiments, the complementary copy can be paired to the template nucleic acid through the use of tag molecules which identify nucleic acid pairs.

In certain embodiments of the present invention, the tag is a molecule or nucleic acid sequence that is incorporated into an oligonucleotide primer used to generate the nucleic acid pair. In some embodiments, the tag is a molecule or nucleic acid sequence that is incorporated into a partner oligonucleotide. In some embodiments, the template nucleic acid can be covalently coupled to a partner oligonucleotide. Thus, in such embodiments, the oligonucleotide primer and the partner oligonucleotide each comprise a unique or distinct tag sufficient to identify the template nucleic acid and the complementary copy.

As used herein, the terms "partner oligonucleotide," "oligonucleotide tag" and like terms refer to an oligonucleotide which comprises a unique tag sufficient to identify the template nucleic acid and the complementary copy. Alternatively, the tag can be a tag that is distinct enough from other tags to distinguish it from the other tags.

Embodiments utilizing tags are especially useful in methods and compositions that include or comprise a plurality of the same, similar and/or different nucleic acids. Such embodiments are often referred to as multiplex embodiments. In these multiplex embodiments, the methods are performed using and the compositions comprise a population of nucleic acids. In some embodiments, the population of nucleic acids may be divided into one or more subpopulations.

In particular embodiments, microspheres or beads useful for detecting methylation can be arrayed or otherwise spatially distinguished. Exemplary bead-based arrays that can be used in the invention include, without limitation, those in which beads are associated with a solid support as described in U.S. Pat. No. 6,355,431 B1, US 2002/0102578 and PCT Publication No. WO 00/63437, each of which is incorporated herein by reference in its entirety.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "Microsphere Detection Guide" from Bangs Laboratories, Fishers Ind. is a helpful guide.

The beads need not be spherical; irregular particles may be used. In addition, the beads may be porous, thus increasing the surface area of the bead available for assay. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used. An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Any of a variety of arrays known in the art can be used in the present invention. For example, arrays that are useful in the invention can be non-bead-based. A particularly useful array is an Affymetrix™ GeneChip™ array or other arrays produced by photolithographic methods such as those described in WO 00/58516; U.S. Pat. Nos. 5,143,854, 5,242, 974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in WO 99/36760, each of which is incorporated herein by reference. A spotted array can also be used in a method of the invention. An exemplary spotted array is a CodeLink™ Array available from Amersham Biosciences. Another array that is useful in the invention is one manufactured using inkjet printing methods such as SurePrint™ Technology available from Agilent Technologies.

Probes used in an array can be specific for the methylated allele of a locus, the non-methylated allele of the locus or both alleles. Specificity can result, for example, from complementarity of a nucleic acid probe to the sequence of one or both alleles or to the sequence of a detection probe that is specifically modified in the presence of one or both alleles (for example, via bisulfite treatment). Specificity can also be a function of probe modification that occurs in a target-specific fashion. For example, a probe that binds both alleles of a locus can be extended to incorporate a different nucleotide in a template-directed polymerase extension event depending upon the allele that is hybridized to the probe. Examples of probe modification reactions that can be used to provide specificity for particular alleles are known in the art as described, for example, in US 2005/0181394, which is incorporated herein by reference. A probe used in an array can also be specific for other detection probes that are modified in the presence of the methylated or non-methylated allele of a locus, such as the address sequence of a ligation probe used in the DNA methylation detection method as described, for example, in Bibikova et al., *Genome Research*, 16:383-393 (2006). Arrays that achieve specificity via probes with sequences that are complementary to address sequences rather than to the sequence of methylated loci are referred to as universal arrays.

DNA Samples

A DNA sample used in a method set forth herein can be obtained from any biological fluid, cell, tissue, organ or portion thereof, that contains genomic DNA suitable for methylation detection. The DNA sample can be derived from a biological source by isolation techniques or amplification techniques or a combination of these techniques. A sample can include or be suspected to include a neoplastic cell, such as a cell from the colon, rectum, breast, ovary, prostate, kidney, lung, blood, brain or other organ or tissue that contains or is suspected to contain a neoplastic cell. The methods can use samples present in an individual as well as samples obtained or derived from the individual. For example, a sample can be a histologic section of a specimen obtained by biopsy, or cells that are placed in or adapted to tissue culture or cells that are stored, for example, as fresh frozen paraffin embedded samples. A sample further can be a subcellular fraction or extract, or a crude or substantially pure nucleic acid molecule. It will be appreciated, however, that samples need not originate from humans. In some embodiments, samples can comprise a composition of nucleic acids obtained from one or more organisms.

A sample can be obtained in a variety of ways known in the art. Samples may be obtained according to standard techniques from all types of biological sources that are usual sources of nucleic acids including, but not limited to cells or cellular components which contain nucleic acids, cell lines, biopsies, bodily fluids such as blood, sputum, stool, urine, cerebrospinal fluid, ejaculate, tissue embedded in paraffin such as tissue from eyes, intestine, kidney, brain, heart, prostate, lung, breast or liver, histological object slides, and all possible combinations thereof. In preferred embodiments, the nucleic acids comprise genomic DNA. Such genomic DNA can be amplified or copied such that the sequence information and methylation state of the genomic DNA is converted to another nucleic acid form such as RNA, cDNA, cRNA or the like.

In some embodiments, the methylation status can be determined using a bead array from a company such as Illumina, Inc. (San Diego, Calif.). However, other types of DNA arrays, such as those manufactured by Affymetrix, Inc. (San Jose, Calif.) are also contemplated. The data imported into a methylation analysis algorithm can be obtained by any method, including those described above. Those skilled in the art will know or be able to determine appropriate format in which to place methylation data for importation and analysis into a methylation analysis algorithm. Similarly those skilled in the art will know or be able to determine how to modify any of a variety of methylation analysis algorithms to include a method for determining standard deviation of methylation levels or a method for comparing methylation levels in accordance with the teaching provided herein.

Diagnostic and Prognostic Methods

The methods set forth herein exploit the potential of genomic methylation of CpG dinucleotides and other genomic DNA loci as indicators of the presence of a condition in an individual and provides a reliable diagnostic and/or prognostic method applicable to any condition associated with altered levels or patterns of genomic methylation of CpG dinucleotides or other loci. The methods can be applied to the characterization, classification, differentiation, grading, staging, diagnosis, or prognosis of a condition characterized by a pattern of one or more methylated genomic CpG dinucleotide sequences that is distinct from the pattern of one or more methylated genomic CpG dinucleotide sequences exhibited in the absence of the condition. For example, a method set forth herein can be used to determine whether the methylation level for a sample suspected of being affected by a disease or condition is the same or different compared to a sample that is considered "normal" with respect to the disease or condition.

In particular embodiments, the methods can be directed to diagnosing an individual with a condition that is characterized by a methylation level and/or pattern of methylation at particular loci in a test sample that are distinct from the methylation level and/or pattern of methylation for the same loci in a sample that is considered normal or for which the condition is considered to be absent. The methods can also be used for predicting the susceptibility of an individual to a condition that is characterized by a level and/or pattern of methylated loci that is distinct from the level and/or pattern of methylated loci exhibited in the absence of the condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

Abnormal methylation of CpG islands associated with tumor suppressor genes can cause decreased gene expression. Increased methylation of such regions can lead to progressive reduction of normal gene expression resulting in the selection of a population of cells having a selective growth advantage. Conversely, decreased methylation (hypomethylation) of oncogenes can lead to modulation of normal gene expression resulting in the selection of a population of cells having a selective growth advantage.

Accordingly, in particular embodiments a disease or condition to be analyzed with respect to methylation levels is cancer. Exemplary cancers that can be evaluated using a method of the invention include, but are not limited to cancer of the breast, prostate, lung, bronchus, colon, rectum, urinary bladder, kidney, renal pelvis, pancreas, oral cavity or pharynx (Head & Neck), ovary, thyroid, stomach, brain, esophagus, liver, intrahepatic bile duct, cervix, larynx, soft tissue such as heart, testis, gastro-intestinal stroma, pleura, small intestine, anus, anal canal and anorectum, vulva, gallbladder, bones, joints, hypopharynx, eye or orbit, nose, nasal cavity, middle ear, nasopharynx, ureter, peritoneum, omentum, or mesentery. Other cancers that can be evaluated include, for example, Chronic Myeloid Leukemia, Acute Lymphocytic Leukemia, Malignant Mesothelioma, Acute Myeloid Leukemia, Chronic Lymphocytic Leukemia, Multiple Myeloma, Gastrointestinal Carcinoid Tumors, Non-Hodgkin Lymphoma, Hodgkin Lymphoma or Melanomas of the skin.

With particular regard to cancer, changes in DNA methylation have been recognized as one of the most common molecular alterations in human neoplasia. Hypermethylation of CpG islands located in the promoter regions of tumor suppressor genes is a well-established and common mechanism for gene inactivation in cancer (Esteller, *Oncogene* 21(35): 5427-40 (2002)). In contrast, a global hypomethylation of genomic DNA is observed in tumor cells; and a correlation between hypomethylation and increased gene expression has been reported for many oncogenes (Feinberg, *Nature* 301(5895): 89-92 (1983), Hanada, et al., *Blood* 82(6): 1820-8 (1993)). Cancer diagnosis or prognosis can be made in a method set forth herein based on the methylation state of particular sequence regions of a gene including, but not limited to, the coding sequence, the 5'-regulatory regions, or other regulatory regions that influence transcription efficiency.

The prognostic methods set forth herein are useful for determining if a patient is at risk for recurrence. Cancer recurrence is a concern relating to a variety of types of cancer. The prognostic methods can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

A reference genomic DNA (for example, gDNA considered "normal") and a test genomic DNA that are to be compared in a diagnostic or prognostic method, can be obtained from different individuals, from different tissues, and/or from different cell types. In particular embodiments, the genomic DNA samples to be compared can be from the same individual but from different tissues or different cell types, or from tissues or cell types that are differentially affected by a disease or condition. Similarly, the genomic DNA samples to be compared can be from the same tissue or the same cell type, wherein the cells or tissues are differentially affected by a disease or condition.

A reference genomic DNA, to which a test genomic DNA will be compared in a diagnostic or prognostic method, can be obtained from age-matched normal classes of adjacent tissues, or with normal peripheral blood lymphocytes. The reference gDNA can be obtained from non-tumorous cells from the same tissue as the tissue of the neoplastic cells to be tested. The reference DNA can be obtained from in vitro cultured cells which can be manipulated to simulate tumor cells, or can be manipulated in any other manner which yields methylation levels which are indicative of cancer or another condition of interest.

It is understood that a reference methylation level to which a test methylation level is compared in a diagnostic or prognostic method will typically correspond to the level of one or more methylated genomic CpG dinucleotide sequences present in a corresponding sample that allows comparison to the desired phenotype. For example, in a diagnostic application a reference level can be based on a sample that is derived from a cancer-free origin so as to allow comparison to the biological test sample for purposes of diagnosis. In a method of staging a cancer it can be useful to apply in parallel a series of reference levels, each based on a sample that is derived from a cancer that has been classified based on parameters established in the art, for example, phenotypic or cytological characteristics, as representing a particular cancer stage so as to allow comparison to the biological test sample for purposes of staging. In addition, progression of the course of a condition can be determined by determining the rate of change in the level or pattern of methylation of genomic CpG dinucleotide sequences by comparison to reference levels derived from reference samples that represent time points within an established progression rate. It is understood, that the user will be able to select the reference sample and establish the reference level based on the particular purpose of the comparison.

EQUIVALENTS

The foregoing written specification is considered to be sufficient to enable one skilled in the art to practice the present embodiments. The foregoing description and Examples detail certain preferred embodiments and describes the best mode contemplated by the inventors. It will be appreciated, however, that no matter how detailed the foregoing may appear in text, the present embodiments may be practiced in many ways and the present embodiments should be construed in accordance with the appended claims and any equivalents thereof.

The term "comprising" is intended herein to be open-ended, including not only the recited elements, but further encompassing any additional elements.

What is claimed is:

1. An array comprising:
   a) a solid support with a plurality of sites configured for single molecule detection; and
   b) a plurality of nucleic acid pairs coupled to the plurality of sites such that different pairs are spatially resolved from each other on the solid support, wherein each nucleic acid pair comprises a template nucleic acid and a complementary copy of said template nucleic acid, the template nucleic acid and complementary copy being physically tethered by an oligonucleotide capable of forming a hairpin loop.

2. The array of claim 1, wherein the solid support comprises a material selected from the group consisting of: plastic, ceramic, glass, polystyrene, methylstyrene, acrylic polymers, paramagnetic materials, thoria sol, carbon graphite, titanium dioxide, sepharose, cellulose, nylon, cross-linked micelles and teflon.

3. The array of claim 1, wherein the orientation of the template nucleic acid and the complementary copy of the nucleic acid pair forms an imperfect inverted repeat.

4. The array of claim 1, wherein each nucleic acid pair comprises a free 3' end and a free 5' end.

5. The array of claim 4, wherein the free 3' end comprises a 3' adapter sequence.

6. The array of claim 5, wherein the 3' adapter sequence comprises a sequence complementary to a capture probe.

7. The array of claim 4, wherein the free 5' end comprises a 5' adapter sequence.

8. The array of claim 7, wherein the 5' adapter sequence comprises a sequence complementary to a capture probe.

9. The array of claim 1, wherein the template nucleic acid comprises a cytosine residue.

10. The array of claim 1, wherein the template nucleic acid comprises a bisulfate-converted polynucleotide.

11. The array of claim 10, wherein the bisulfite-converted polynucleotide comprises a uracil residue.

12. The array of claim 1, wherein the complementary copy of said template nucleic acid comprises a bisulfite-resistant polynucleotide.

13. The array of claim 12, wherein the bisulfite-resistant polynucleotide comprises a bisulfite-resistant cytosine analog selected from the group consisting of 5-ethyl cytosine, 5-methyl cytosine, 5-fluoro cytosine, 5-bromo cytosine, 5-iodo cytosine, 5-chloro cytosine, 5-trifluoromethyl cytosine, and 5-aza cytosine.

14. The array of claim 12, wherein the bisulfite-resistant cytosine analog is 5-methyl cytosine.

15. The array of claim 1, wherein the template nucleic acid is single-stranded.

16. The array of claim 1, wherein the complementary copy is single-stranded.

17. The array of claim 1, wherein the template nucleic acid comprises DNA.

18. An array comprising:
   a) a solid support with a plurality of sites; and
   b) a plurality of nucleic acid pairs coupled to the plurality of sites, wherein each nucleic acid pair comprises:
      (i) a template nucleic acid comprising a cytosine residue,
      (ii) a complementary copy of said template nucleic acid comprising a bisulfite-resistant cytosine analog, and
      (iii) an oligonucleotide capable of forming a hairpin loop physically tethering the template nucleic acid and the complementary copy.

19. The array of claim 18, wherein the template nucleic acid is single-stranded.

20. The array of claim 18, wherein the plurality of sites comprises a plurality of sites configured for single molecule detection.

* * * * *